United States Patent [19]

Holland

[11] 3,983,107

[45] Sept. 28, 1976

[54] HYPOLIPIDEMIC ALKENESULFONAMIDES

[75] Inventor: Gerald F. Holland, Old Lyme, Conn.

[73] Assignee: Pfizer Inc., New York, N.Y.

[22] Filed: Nov. 6, 1974

[21] Appl. No.: 521,445

Related U.S. Application Data

[63] Continuation-in-part of Ser. No. 422,088, Dec. 5, 1973, abandoned.

[52] U.S. Cl. .......................... 260/240 J; 260/240 D; 260/240 R; 260/239 B; 260/239 BA; 260/247.1 R; 260/283 SA; 260/293.73; 260/294.8 F; 260/326.82; 260/553 D; 260/553 DA; 424/244; 424/246; 424/248; 424/258; 424/263; 424/267; 424/274; 424/321

[51] Int. Cl.² ..................................... C07D 211/06

[58] Field of Search ......... 260/240 J, 240 D, 240 R, 260/553 D, 553 DA, 239 BA, 283 SA, 293.73

[56] References Cited
UNITED STATES PATENTS

| | | | |
|---|---|---|---|
| 2,979,437 | 4/1961 | McLamore | 260/553 D |
| 3,426,017 | 2/1969 | Jucker et al. | 260/239 BA |
| 3,705,151 | 12/1972 | Weber et al. | 260/239 BA |
| 3,847,938 | 11/1974 | Weber et al. | 260/283 SA |

OTHER PUBLICATIONS

Hartig, J. Prakt. Chem. 33, (1966), pp. 215, 221.

*Primary Examiner*—Arthur P. Demers
*Attorney, Agent, or Firm*—Connolly and Hutz

[57] ABSTRACT

Method for lowering blood liped levels in mammals, using certain derivatives of N-carbamoyl-2-phenylethenesulfonamide, many of which are novel.

6 Claims, No Drawings

HYPOLIPIDEMIC ALKENESULFONAMIDES

CROSS-REFERENCE TO RELATED APPLICATIONS

This application is a continuation-in-part of co-pending application, Ser. No. 422,088, filed Dec. 5, 1973, now abandoned.

BACKGROUND OF THE INVENTION

1. Field of the Invention

This invention relates to a new method for reducing elevated serum lipid levels in mammals. Atherosclerosis, which is a form of arteriosclerosis, is rapidly becoming recognized as a major health problem today. The disease is characterized by deposition of lipids in the aorta, and in the cornonary, cerebral and peripheral arteries of the lower extremities. As the deposits increase, the danger of thrombus formation and occlusion exists. Although the origins of atherosclerosis are not fully understood, it has been observed that many people suffering from this disease exhibit elevated plasma lipid protein levels, of which cholesterol and triglycerides are major components. Despite the fact that dietary habits can contribute to lowering plasma lipoprotein levels, several therapeutic agents, such as estrogens, thyroxin analogues and sitosterol preparations have been employed for this purpose. Recently, ethyl 2-(p-chlorophenoxy)isobutyrate (clofibrate) has been shown to be an effective agent for reducing elevated triglyceride levels in humans.

This invention also relates to certain novel chemical compounds, useful for reducing serum lipid levels in mammals. These novel chemical compounds are derivatives of N-carbamoyl-2-phenylethenesulfonamide, which is also known as styrenesulfonylurea.

2. Description of the Prior Art

Arenesulfonamides, substituted on the nitrogen atom by a monosubstituted carbamoyl group (arenesulfonylureas), are a well-known class of organic compounds, some of which are known to have hypoglycemic properties. For example, N-(N-n-propylcarbamoyl)-p-chlorobenzenesulfonamide (chlorpropamide) and N-(N-n-butylcarbamoyl)-p-toluenesulfonamide (tolbutamide) are clinically-useful oral antidiabetic agents. However, there is a paucity of references in the literature to sulfonylureas in which the nitrogen atom of the urea moiety remote from the sulfonyl group carries two substituents other than hydrogen.

2-Phenylethenesulfonamides, substituted on the nitrogen atom by a carbamoyl group (styrenesulfonylureas), are not well known in the chemical or patent literature, although U.S. Pat. No. 2,979,437, issued Apr. 11, 1961, discloses a series of aralkenesulfonylureas with hypoglycemic properties.

SUMMARY OF THE INVENTION

It is an object of this invention to provide a new method for reducing elevated plasma lipid levels in mammals. The method comprises administering to a hyperlipidemic mammal an effective amount of a compound selected from 2-phenylethenesulfonamide derivatives of the formulae:

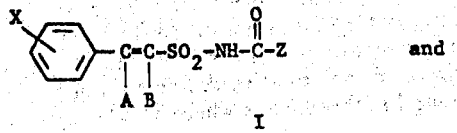

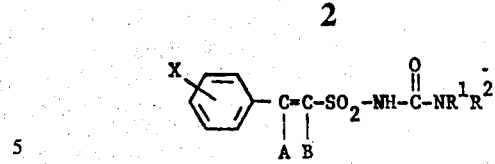

and the pharmaceutically-acceptable salts thereof;

wherein X is selected from the group consisting of hydrogen, fluoro, chloro, bromo, trifluoromethyl, alkyl having from one to four carbon atoms and alkoxy having from one to four carbon atoms;

A and B are each selected from the group consisting of hydrogen, methyl, ethyl and phenyl;

Z is selected from the group consisting of pyrrolidino, morpholino, thiomorpholino, 1,2,5,6-tetrahydropyridino, 1,2,3,4-tetrahydroisoquinolino, azacyclo heptan-1-yl, azacyclooctan-1-yl, 3-azabicyclo[3.2.2]nonan-3-yl, piperidino, 4-hydroxypiperidino, 4-methoxy piperidino, 4-carboxypiperidino, 4-phenylpiperidino, alkylpiperidino having from one to three carbon atoms in said alkyl group, (phenylalkyl)-piperidino having from one to five carbon atoms in said alkyl group and ([substituted phenyl]alkyl)piperidino having from one to five carbon atoms in said alkyl group, said substituted phenyl being substituted by a moiety selected from the group consisting of hydroxy, alkyl having from one to four carbon atoms and alkoxy having from one to four carbon atoms;

and $R^1$ and $R^2$ are each selected from the group consisting of hydrogen, alkyl having from one to ten carbon atoms, alkenyl having from three to six carbon atoms, cycloalkyl having from three to seven carbon atoms, phenylalkyl having from one to two carbon atoms in said alkyl group, carboxyalkyl having from one to seven carbon atoms in said alkyl group, alkoxycarbonylalkyl having from one to two carbon atoms in said alkoxy group and having from one to seven carbon atoms in said alkyl group, bicyclo[2.2.1]hept-2-en-5-ylmethyl, 7-oxabicyclo[2.2.1]heptan-2-ylmethyl, bicyclo[2.2.1]heptan-2-ylmethyl, phenyl and phenyl substituted by a moiety selected from the group consisting of fluoro, chloro, bromo, nitro, alkyl having from one to four carbon atoms and alkoxy having from one to four carbon atoms; provided that $R^1$ and $R^2$ are not both hydrogen.

However, the preferred hypolipidemic agents of this invention are the compounds of formulae I and II, wherein X is selected from the group consisting of hydrogen, chloro and methyl; A and B are each selected from the group consisting of hydrogen, methyl and ethyl; and Z, $R^1$ and $R^2$ are as defined hereinbefore.

Particularly preferred hypolipidemic agents of this invention of formula I are those compounds of formula I, wherein X is selected from the group consisting of hydrogen, chloro and methyl, A and B are each hydrogen and Z is selected from the group consisting of 4-(ω-phenylalkyl)-piperidino having from one to five carbon atoms in said alkyl group and 4-(ω-[substituted phenyl]alkyl)-piperidino having from one to five carbon atoms in said alkyl group, said substituted phenyl being substituted by a moiety selected from the group consisting of hydroxy, alkyl having from one to four carbon atoms and alkoxy having from one to four carbon atoms. In this context, the terms ω-phenylalkyl and ω-[substituted phenyl]alkyl are intended to refer to straight-chain alkyl groups with a phenyl or a substituted phenyl group, respectively, on the terminal carbon atom of the alkyl group, e.g. 2-phenylethyl, 3-phenylpropyl and 5-phenylpentyl. The preferred value for X is hydrogen. Expecially valuable compounds of formula I are those compounds wherein X, A and B are each hydrogen and Z is the said 4-(ω-phenylalkyl)-piperidino.

Other particularly preferred hypolipidemic agents of formula I are those compounds of formula I, wherein X is selected from the group consisting of hydrogen, chloro and methyl, A and B are each hydrogen and Z is 1,2,3,4-tetrahydroisoquinolino.

Particularly preferred hypolipidemic agents of formula II are those compounds of formula II, wherein X, A, B and $R^1$ are hydrogen and $R^2$ is either the said alkyl, expecially n-butyl, or the said carboxyalkyl, especially carboxymethyl.

Other particularly preferred hypolipidemic agents of formula II, are those compounds of formula II, wherein X, A and B are each hydrogen and $R^1$ and $R^2$ are each the said alkyl, especially n-butyl.

Individual compounds of the instant invention which are of particular value are:

N-(N-n-butylcarbamoyl)-2-phenylethenesulfonamide,

N-(N-[carboxymethyl]carbamoyl)-2-phenylethenesulfonamide,

N-(4-[3-phenylpropyl]piperidinocarbonyl)-2-phenylethenesulfonamide

N-(1,2,3,4-tetrahydroisoquinolinocarbonyl)-2-phenylethenesulfonamide.

Many of the hypolipidemic agents of this invention are novel, and as such they form an important embodiment of the invention. Thus, all the compounds of formula I are novel. The compounds of formula II are novel provided that when either $R^1$ or $R^2$ is hydrogen, the said alkyl, the said alkenyl, the said cycloalkyl, phenyl or the said substituted phenyl, the other $R^1$ or $R^2$ is other than hydrogen or the said alkyl.

DETAILED DESCRIPTION OF THE INVENTION

In accordance with the invention, the compounds of formulae I and II are conveniently synthesized from an alkenesulfonamide of formula III, wherein X, A and B are as previously defined, by one of several methods. Five such methods, designated hereinafter as Methods A, B, C, D and E, are now to be discussed and described in detail.

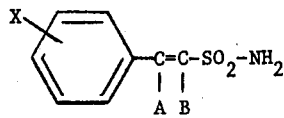

III

Method A comprises the reaction of a compound of formula III with an organic isocyanate of formula $R^1$—N=C=O, in the presence of a base. The reaction is usually carried out by contacting the reagents in an appropriate solvent, at a temperature normally in the range from about 25° to about 120°C, and preferably from about 60° to about 80°C. Appropriate solvents which can be used are those which will serve to dissolve at least one of the reactants and which do not adversely interact with either the reactants or the product. Examples of such solvents are ethers, such as diethyl ether, tetrahydrofuran 1,2-dimethoxyethane; chlorinated hydrocarbons, such as chloroform, methylene chloride and 1,2-dichloroethane; lower aliphatic ketones, such as acetone, methyl ethyl ketone and methyl isobutyl ketone; esters, such as ethyl acetate and butyl acetate; and tertiary amides, such as N,N-dimethylformamide, N,N-dimethylacetamide and N-methylpyrrolidone. A wide variety of bases, belonging to both the organic and inorganic types can be used in this process, since it appears that the primary function of the basic agent is to form a salt of the sulfonamide reactant. Bases which are used include tertiary amines, such as triethylamine, tributylamine, N,N-dimethylaniline, pyridine, quinoline, N-methylmorpholine and 1,5-diazabicyclo[4.3.0]-non-5-ene; alkali metal hydroxides, such as sodium hydroxide and potassium hydroxide; alkali metal alkoxides, such as sodium methoxide, potassium methoxide and sodium ethoxide; metal hydrides such as sodium hydride and calcium hydride; metal carbonates, such as sodium carbonate and potassium carbonate; and alkali metals such as sodium and potassium. In most instances one molar equivalent of base, based on the sulfonamide used, is employed, but amounts smaller or larger than one molar equivalent can successfully be used. Although it is common to aid a one-to two-fold excess of isocyanate, this is not essential, and equimolar proportions are sometimes used, particularly in those cases where it would be inconvenient to remove the excess of isocyanate from the product. In fact, it is possible to employ an excess of sulfonamide; in which case some sulfonamide remains at the end of the reaction. When working at about 80°C., reaction times of a few hours, for example 2 hours, are usually used. A particularly convenient means of isolating the product involves adding the reaction mixture to an excess of dilute aqueous acid. If this causes the product to precipitate, it is filtered off directly. Alternatively it is extracted into a water-immiscible organic solvent, which is then separated off and evaporated, leaving the crude product. In many cases the crude product is essentially pure, but, if desired, it can be purified further by methods known in the art.

As will be appreciated by one skilled in the art, it is possible to pre-form a salt of the starting sulfonamide, which is then treated with the isocyanate in a subsequent step. In this case the same method and conditions discussed above are operative in the second step of this two-step process.

The starting isocyanates used in Method A are either items of commerce, or they are readily prepared by reaction of the appropriate amine with phosgene, using the method taught by Shriner, Horne and Cox in Organic Synthesis, Collective Volume II, 453 (1943).

Method B comprises the reaction of a compound of formula III with a carbamoyl chloride of formula Z—C(=O)—Cl or $R^1R^2N$—C(=O)—Cl, in the presence of a base. In a typical procedure, approximately one molar equivalent of the carbamoyl chloride is added to a solution or suspension of the sulfonamide of formula III in an appropriate solvent, in the presence of the base. The same solvents and bases enumerated above under Method A are operative in this process, and approximately one molar equivalent is commonly employed. On the other hand, larger amounts of base can be used in those cases wherein the excess of base will not adversely affect the reactants or products. Indeed, an excess is commonly used when the base is not soluble in the reaction medium. The reaction temperature and reaction time vary according to a variety of factors, such as the reactivity and concentrations of the reagents and the solubility of the reagents in the particular solvent system chosen. However, the reaction is usually carried out in the temperature range from about 40° to 120°C., and preferably from about 50° to about 80°C. At the latter temperatures, reaction times of a few hours, for example 4 hours, are typically used. The product can be isolated using the methods discussed above under Method A.

An alternate variation for Method B, which approximates the Schotten-Baumann procedure, and which is convenient in certain instances, comprises adding the carbamoyl chloride to a solution of the sulfonamide in water, at about ambient temperature, with the pH being maintained within the range from about 7.0 to about 12.0 during and after the addition. At the end of the reaction, which typically requires about one hour, the reaction mixture is acidified. If the product precipitates it is filtered off. Alternatively it can be extracted into a water-immiscible organic solvent, which is then separated off, and evaporated, leaving the crude product.

The carbamoyl chlorides used in Method B are either items of commerce, or they are readily prepared by reaction of the appropriate amine with phosgene, using methods discussed by Peterson in Houben-Weyl's "Methoden der Organischen Chemie," 8, 115–118 (1962).

In method C, a sulfonamide of formula III reacts with a urea derivative of formula $R^1NH-CO-NR^3R^4$, in the presence of a base, wherein $R^3$ is selected from the group consisting of alkyl having from one to six carbon atoms, alkenyl having from three to seven carbon atoms, aryl, substituted aryl, heteroaryl and substituted heteroaryl, and $R^4$ is selected from the group consisting of hydrogen, cycloalkyl having from three to eight carbon atoms, benzyl, phenylethyl and $R^3$, wherein each substituted moiety is substituted by up to three members selected from the group consisting of chloro, fluoro, bromo, nitro, alkyl having from one to four carbon atoms and alkoxy having from one to four carbon atoms. Typical examples of aryl groups are phenyl and naphthyl, and typical examples of heteroaryl groups are pyridyl, thiazolyl, oxazolyl and quinolyl. A particularly convenient configuration for the urea moiety used in this Method is that wherein $R^3$ and $R^4$ are each phenyl. The reaction is carried out by contacting sulfonamide and urea using exactly the same solvents, reaction parameters, bases and reactant ratios, etc., described hereinbefore for the operation of Method A. Indeed it is postulated that, under the influence of base, the urea of formula $R^1NH-CO-NR^3R^4$ acts as a source of isocyanate. However, this is a matter of theory, and in no way affects the conduct of the reaction.

The substituted ureas of formula $R^1NH-CO-NR^3R^4$ are prepared from the appropriate amine of formula $R^1NH_2$ and carbamoyl chloride of formula $Cl-CO-NR^3R^4$, using the procedure of McManus et al. (Journal of Medicinal Chemistry, 8, 766 ([1965]) and minor variations thereof. The carbamoyl chlorides of formula $Cl-CO-NR^3R^4$ are obtained from the appropriate amine of formula $HNR^3R^4$ and phosgene as indicated in Method B.

Method D comprises the reaction of a sulfonyl isocyanate of formula IV, wherein X, A and B are as defined previously, with the appropriate amine of formula HZ or $HNR^1R^2$. The reaction is usually carried out by contacting the isocyanate and amine in a reaction-inert, organic solvent, at or about ambient temperature, until the reaction is substantially complete. Reaction times of a few hours, e.g. from about 1 hour to about 12 hours, are commonly used. The same solvents enumerated in method A are useful in the instant process, and the product is recovered by methods discussed above under Method A. Although the ratio of isocyanate to amine is not critical, and use of an excess of either component will successfully lead to product, it is usual to employ a small excess of amine, for example a one-fold excess.

The starting sulfonyl isocyanates are prepared from the corresponding sulfonamide of formula III, by reaction with an excess of oxalyl chloride, followed by pyrolysis of the oxamic acid chloride intermediate thus obtained. Such transformations are well-known in the art. See, for example, Franz and Osuch, *Journal of Organic Chemistry*, 29, 2592 (1964). It is a convenient procedure in many instances to use the sulfonyl isocyanate in the solvent in which it is prepared, without isolation. Moreover, if desired, the oxamic acid chloride can be treated directly with the amine, and this will successfully lead to the formation of a compound of formula I or II.

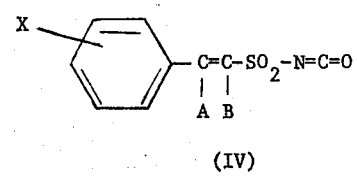

(IV)

Method E comprises the reaction of an amine of formula HZ or $HNR^1R^2$ with a compound of formula V, wherein Z, $R^1$, $R^2$, $R^3$ and $R^4$ are as defined previously. The reaction is usually conducted by heating the two reactants together

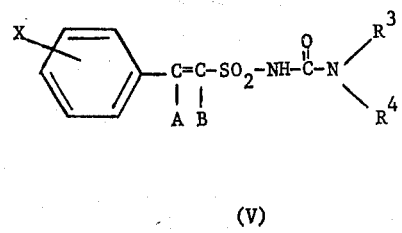

(V)

in a reaction-inert organic solvent, which is usually a polar, organic solvent which serves to dissolve the reactants. Appropriate solvents are, for example, lower alkanols, such as methanol, ethanol and n-butanol; glycols, such as ethylene glycol and propylene glycol; ethers, such as dioxane and 1,2-dimethoxyethane; acetonitrile; and tertiary amides, such as N,N-dimethylformamide, N,N-dimethylacetamide and N-methylpyrrolidone. The temperature and duration of reaction required to complete the conversion to product are interrelated. At lower temperatures longer periods are required, while at higher temperatures the reaction is complete in a shorter time. Moreover, the rate of reaction depends on the nucleophilicity of the reactant amine and the efficacy of the leaving group. In any event, reaction times of a few hours are usually used, and the reaction is normally conducted in the range from about 50° to about 150°C and preferably in the range from about 80° to 100°C. At around 100°C. a reaction time of about 5 hours is commonly used. If desired, the starting compound of formula V can be used in the form of a salt, for example an alkali metal salt, such as a potassium salt. Alternatively, the compound of formula V can be introduced into the reaction medium in the form of a salt, which is then neutralized by the addition of an alkanoic acid, such as acetic acid. Although the reactants in this Method are normally combined in equimolar proportions, the ratio of reactant is not critical and an excess of either component can successfully be used. The product can be isolated by evaporating the solvent in vacuo, and then partitioning the residue between dilute aqueous acid and a water-immiscible organic solvent. Evaporation of the organic solvent then affords the crude product, which can be purified further by well-known methods, if desired.

In certain instances, Method D is carried out in the absence of a solvent. In this case the sulfonamide of formula V and the amine are simply heated together, until the conversion to product is substantially complete. As indicated above, reaction times of a few hours, e.g. about 5 hours are used, and the reaction is usually conducted at a temperature in the range from about 50° to about 150°C., and preferably in the range from about 80° to about 100°C. This particular variation is convenient when the compound of formula V and the amine exist in the liquid phase at the reaction temperature.

Although the detailed course of Method D has not been elucidated, it is hypothesized that some sulfonyl isocyanate of formula IV is generated in situ during the course of the reaction.

Preferred values for $R^3$ are alkyl having from one to six carbon atoms, phenyl and phenyl substituted by up to two moieties selected from the group consisting of fluoro, chloro, bromo, nitro, alkyl having from one to four carbon atoms and alkoxy having from one to four carbon atoms, and preferred values for $R^4$ are hydrogen and $R^3$. Particularly preferred starting materials of formula V, are those wherein $R^3$ and $R^4$ are each phenyl.

The compounds of formula IV are prepared by reaction of the appropriate sulfonamide of formula III with a carbamoyl chloride of formula $Cl-CO-NR^3R^4$, using the procedure discussed under Method B.

As will be appreciated by one skilled in the art, not all of the Methods A, B, C, and D are equally applicable to the synthesis of all the compounds of formulae I and II. For example, Methods A and C are suitable only for preparing compounds of formula II, wherein either $R^1$ or $R^2$ is hydrogen. In an individual case, the skilled artist will select that synthetic method which is most appropriate, based on such factors as, for example, the feasibility of the chemical reactions, the availability of the starting materials, the reactivity of the starting materials, the stability of the reagents and products and the scale of the reaction to be run.

A further alternate synthetic method which is used specifically for those compounds of formula II, wherein either $R^1$ or $R^2$ is carboxyalkyl, is the hydrolysis of the corresponding compound of formula II, wherein either $R^1$ or $R^2$ is alkoxycarbonylalkyl. Because of the stability characteristics of the said compounds of formula II, and ease of operation, the instant hydrolysis is usually carried out using basic conditions. In many instances it is sufficient simply to dissolve the ester in dilute sodium hydroxide solution, store the solution at ambient temperature for a few hours, and then acidify the solution. Either the product precipitates in a form which can be filtered off, or it is extracted into a water-immiscible solvent such as ethyl acetate. The solvent is then dried and evaporated in order to recover the crude product. However, a variety of water-miscible co-solvents, such as lower alkanols, for example methanol and ethanol, or acetone, can be added to aid dissolution. Furthermore, various other bases known in the art to be useful for alkaline hydrolysis reactions, such as, for example, potassium hydroxide, calcium hydroxide, barium hydroxide, sodium carbonate and potassium carbonate, are equally operative. The basic agent will normally be present to the extent of at least one molar equivalent based on the ester used, but larger amounts, up to about 20 molar equivalents can be used. Although the reaction is commonly conducted at ambient temperature, it is possible to use temperatures in the range from about 0° to about 100°C. The time course of the reaction varies according to the temperature, since the reaction proceeds more quickly as the reaction temperature is increased. However, when the reaction is carried out at about 25° to 50°C., reaction times of several hours, for example overnight, are commonly used.

A still further alternate synthetic method is used for preparation of the compounds of formula I, wherein Z is ([hydroxyphenyl]alkyl)piperidino. The method comprises demethylation of the appropriate compound of formula I, wherein Z is the corresponding ([methoxyphenyl]alkyl)piperidino. The demethylation is carried out by methods known in the art for such a transformation, which do not adversely affect the remainder of the molecule. A particular convenient reagent in this regard is boron tribromide, use of which is discussed by Fieser and Fieser in "Reagents for Organic Synthesis," John Wiley & Sons, Inc., New York, 1967, page 66.

As discussed hereinbefore, the starting reagents used in Methods A, B, C, D, and E are sulfonamides of formula III. These sulfonamides can be prepared from ethene derivatives of formula VI, by either of two methods. The first of these comprises the following sequence of reactions:

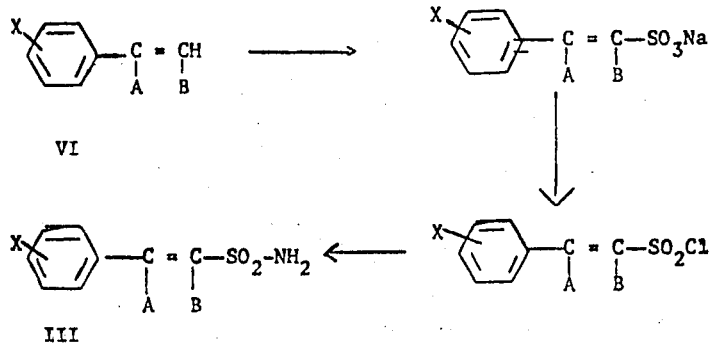

The reagents and conditions used in this sequence are those described, with minor variations, by Bordwell et al. (Journal of the American Chemical Society, 68, 139 [1946]) for the case wherein A, B, and X are each hydrogen. Operation of this reaction sequence is further exemplified in U.S. Pat. No. 2,979,437. The second method used for the conversion of the ethene derivatives of formula VI into the corresponding sulfonamides of formula III, comprises treatment of the said ethene derivatives with sulfuryl chloride in N,N-dimethylformamide, followed by ammonia, using the conditions of Culbertson and Dietz (Journal of the Chemical Society [London], Part C, 992 [1968]), and minor variations thereof.

The ethene derivatives of formula VI are either items of commerce, or they are prepared by either of two general methods, both well-known in the art. The first method comprises a Wittig between a carbonyl compound of formula VII, and the ylid derived from a phosphonium salt of formula $([C_6H_5]_3PCH_2B)^+Y^-$, wherein Y is chloride or bromide as discussed and described by Maercker in "Organic Reactions," 14, 270 (1965), and by Deno et al., in the Journal of the American Chemical Society, 87, 2157 (1965).

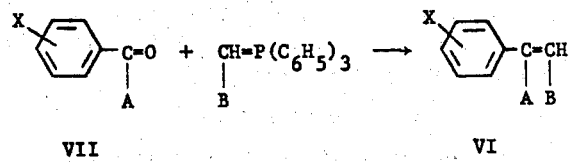

The second method comprises reaction of a carbonyl compound of formula VII with a Grignard reagent of formula $BCH_2MgY$, wherein Y is chloride or bromide, followed by acid-catalysed dehydration of the carbinol so produced, in accordance with procedures discussed by Emerson in Chemical Reviews, 45, 347 (1949), viz:

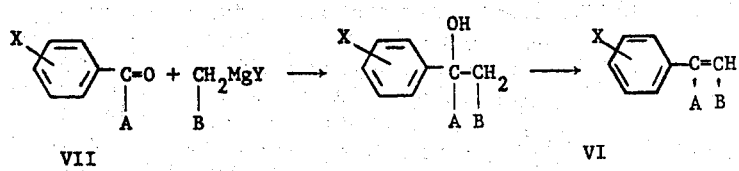

Choice between these two methods will normally be made by the skilled artist on the basis of such factors as the availability of the starting materials, the ease of operation of the method on the scale of reaction contemplated, and the reactivity of the particular reactants.

The carbonyl compounds of formula VII are either items of commerce, or they are prepared by the published literature method. The phosphonium salts of formula $([C_6H_5]_3PCH_2B)^+Y^-$, are conveniently prepared from triphenylphosphine and the appropriate alkyl halide, in accordance with procedures discussed by Maercker, loc. cit., pp 338–393. The alkyl halides are all commercially available.

As will be appreciated by one skilled in the art, many of the alkenesulfonamides of formula II are useful not only as hypolipidemic agents, but also as intermediates for the preparation of hypolipidemic agents. Thus, the compounds of formula II, wherein either $R^1$ or $R^2$ is selected from the group consisting of phenyl and phenyl substituted by a moiety selected from the group consisting of fluoro, chloro, bromo, nitro, alkyl having from one to four carbon atoms and alkoxy having from one to four carbon atoms, are useful as starting materials for Method E, described hereinbefore. Moreover, the compounds of formula II, wherein either $R^1$ or $R^2$ is alkoxycarbonylalkyl, are valuable as starting materials for the preparation by hydrolysis, of the corresponding compounds of formula II, wherein either $R^1$ or $R^2$ is carboxyalkyl.

The hypolipidemic properties of the compounds of the instant invention are readily demonstrated by either of two methods. In the first method, which is essentially the method used by Newman et al. (Lipids, 8, 378 [1973]), the ability of the compounds to inhibit Triton-induced hyperlipidemia in rats is demonstrated. A 300-mg./kg. dose of Triton WR-1339 is injected into normal, Sprague-Dawley, male rats which have been treated orally with the test compound. After further oral dosage with the test compound, the rats are exsanguinated via the abdominal aorta under pentobarbital anesthesia and plasma is obtained from the heparinized blood. Plasma cholesterol concentration is measured using the Auto-Analyser (Technicon Method N-24a), and the value is compared with that obtained from control animals which have received the Triton treatment but no test compound. The plasma cholesterol level in the test-compound fed animals is found to be significantly lower when compared to the levels in animals not receiving the test compound.

In the second method for measuring hypolipidemic properties of the compounds of the instant invention, normal adult, beagle dogs are dosed orally, twice daily, with the test compound, for a period of six days. During the period of the test, the dogs are fed once daily, at 12:00 noon. On the morning of the sixth day, the dogs are bled from the jugular vein and plasma cholesterol is measured by the method adapted for use in the Technicon Auto-Analyser. The level obtained in a given dog is compared with the baseline value for the dog, which has been determined at the start of the test. The plasma cholesterol level is found to be significantly lower at the end of the test, when compared to the baseline value obtained at the beginning of the test.

A characteristic feature of the compounds of the instant invention is their ability to form salts. By virtue of their acidic nature, sulfonylureas have the ability to form salts with basic agents, and all said salts are to be considered a further embodiment of the invention. The salts can be prepared readily and conveniently, for example, simply by contacting the acidic and basic entities, usually in a 1:1 molar ratio, in either an aqueous, non-aqueous or partially aqueous medium, as appropriate. The salts are recovered either by filtration, by precipitation with a non-solvent, by evaporation of the solvent, as appropriate, or, in the case of aqueous solutions, by lyophilization.

Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazobicyclo[4.3.0]non-5-ene; hydroxides, such as sodium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

As will be appreciated by one skilled in the art, the compounds of formula II, wherein either $R^1$ or $R^2$ is carboxyalkyl have the further ability to form carboxylate salts. These salts, which can be formed in exactly the same manner and using exactly the same basic agents, as described above, are also within the purview of the instant invention. In the cases wherein a compound of formula II has two acidic groups, both mono- and di-salts can be prepared. When considering di-salts, the two cationic species can be the same or different.

Although, when contemplating therapeutic use for a compound of the instant invention it is preferable to use a pharmaceutically-acceptable salt, salts other than these can be used for a variety of other purposes. Such purposes include isolating and purifying particular compounds, and interconverting pharmaceutically-acceptable salts with their non-salt counterparts.

The hypolipidemic properties of the alkenesulfonamides of the instant invention make them particularly suitable and valuable for the control of hyperlipidemia in mammals, especially man. For therapeutic use of a compound of this invention, the compound can be administered alone, or, preferably, it can be mixed with pharmaceutically-acceptable carriers or diluents. Said carrier or diluent is chosen on the basis of the intended mode of administration, as well as the solubility and stability of the active ingredient. For example, when considering the oral mode of administration, a hypolipidemic alkenesulfonamide of this invention can be used in the form of tablets, capsules, lozenges, troches, powders, syrups, elixiers, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose and corn starch, and lubricating agents, such as sterotex K, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When the hypolipidemic compounds of this invention are used for the control, that is cure or prophylaxis, of hyperlipidemia in man, the daily dosages will normally be determined by the prescribing physician. Moreover, these dosages will vary according to the age, weight and response of the individual patient, as well as the severity of the patient's symptoms. However, in most instances, an effective daily dosage will be in the range from about 0.5 g. to about 3.0 g., in single or divided doses. On the other hand, it may be necessary to use dosages outside these limits in some cases.

The following examples are provided solely for the purpose of further illustration.

EXAMPLE I

N-(N-Butylcarbamoyl)-1-phenylpropene-2-sulfonamide

To a mixture of 80 ml. of triethylamine and 50 ml. of N,N-dimethylformamide, is added 39.5 g. of 1-phenylpropene-2-sulfonamide followed by 32.5 ml. of n-butyl isocyanate. The mixture is heated at 85°–90°C., with stirring, for 75 minutes. It is cooled to ambient temperature, and then it is poured with stirring into 1 liter of 20% acetic acid. After a further 30 minutes of stirring, the precipitate which forms is filtered off and then dissolved in 300 ml. of hot acetone. The acetone is filtered, and then allowed to cool slowly. The crude product which precipitates is filtered off, washed with aqueous acetone, and allowed to dry. The acetone mother liquors are diluted with water, which causes a second crop of product to precipitate. It is filtered off. The crops are combined and then recrystallized from ethanol, giving 28 g. of N-(N-butylcarbamoyl)-1-phenylpropene-2-sulfonamide, m.p. 135°–136° C.

Analysis—Calcd. for $C_{14}H_{20}N_2O_3S$ (percent): C, 56.74; H, 6.80; N, 9.45. Found: (percent): C, 56.64; H, 6.78; N, 9.27.

EXAMPLE II

Following the procedure of Example I, and reacting either 1-phenylpropene-2-sulfonamide, 2-phenylpropene-1-sulfonamide or 2,2-diphenylethenesulfonamide with the appropriate isocyanate, the following compounds are prepared:

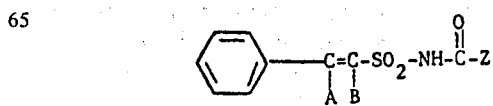

| A | B | Z | m.p. (°C.) | Calc'd (%) C | Calc'd (%) H | Calc'd (%) N | Found (%) C | Found (%) H | Found (%) N |
|---|---|---|---|---|---|---|---|---|---|
| hydrogen | methyl | N-isopropylamino | 191–192 | 55.31 | 6.43 | 9.92 | 55.48 | 6.39 | 9.65 |
| hydrogen | methyl | N-propylamino | 190–192 | 55.31 | 6.43 | 9.92 | 55.61 | 6.51 | 10.19 |
| hydrogen | methyl | N-heptadecylamino | 118.5–122 | 68.26 | 9.82 | 5.69 | 68.18 | 10.12 | 5.66 |
| methyl | hydrogen | N-propylamino | 176–178 | 55.31 | 6.43 | 9.92 | 55.22 | 6.40 | 9.84 |
| methyl | hydrogen | N-cyclohexylamino | 155–158 | 59.60 | 6.88 | 8.69 | 59.91 | 7.21 | 8.62 |
| hydrogen | methyl | N-cyclohexylamino | 142–146 | 59.60 | 6.88 | 8.69 | 59.52 | 7.01 | 8.79 |
| methyl | hydrogen | N-isopropylamino | 163–165 | 55.31 | 6.43 | 9.92 | 55.23 | 6.32 | 9.81 |
| hydrogen | methyl | N-(m-tolyl)amino | 137–139 | 61.81 | 5.49 | 8.48 | 61.94 | 5.49 | 8.34 |
| methyl | hydrogen | N-propylamino | 103–105 | 56.73 | 6.80 | 9.45 | 56.53 | 6.98 | 9.69 |
| hydrogen | hydrogen | N-(ethoxycarbonyl-methyl)amino | 172–174 | 50.00 | 5.16 | 8.97 | 50.12 | 5.13 | 9.02 |
| hydrogen | hydrogen | N-(1-adamantyl)amino | 186–187.5 | 63.32 | 6.71 | 7.77 | 63.29 | 6.81 | 7.67 |
| hydrogen | hydrogen | N-(tert-butyl)amino | 181–182 | 56.74 | 6.80 | 9.45 | 56.48 | 6.85 | 9.49 |
| hydrogen | methyl | N-(1-adamantyl)amino | 168–170 | 64.15 | 7.00 | 7.48 | 64.23 | 6.86 | 7.50 |
| hydrogen | methyl | N-(ethoxycarbonyl-methyl)amino | 181–182 | 51.23 | 5.56 | 8.59 | 51.61 | 5.59 | 8.56 |
| hydrogen | hydrogen | N-(1-methoxycarbonyl-2-phenylethyl)amino | 168–170 | 51.88 | 5.99 | 7.56 | 51.76 | 5.90 | 7.57 |
| hydrogen | hydrogen | N-(1-methoxycarbonyl-3-methylbut-1-yl)amino | 156–158 | 54.23 | 6.26 | 7.91 | 54.12 | 6.25 | 7.94 |
| phenyl | hydrogen | N-isopropylamino | 209–210 | 62.78 | 5.85 | 8.14 | 62.44 | 5.94 | 8.14 |
| phenyl | hydrogen | N-propylamino | 184–186 | 62.78 | 5.85 | 8.14 | 62.56 | 5.89 | 8.00 |

EXAMPLE III

When methyl isocyanate, ethyl isocyanate, isobutyl isocyanate, n-hexyl isocyanate, n-heptyl isocyanate, n-decyl isocyanate, allyl isocyanate, 3,3-dimethylbut-2-yl isocyanate, cyclopropyl isocyanate, cyclopentyl isocyanate, cyclohexyl isocyanate, cycloheptyl isocyanate, phenyl isocyanate, p-fluorophenyl isocyanate, m-bromophenyl isocyanate, m-nitrophenyl isocyanate, p-tolyl isocyanate, p-ethylphenyl isocyanate, p-chlorophenyl isocyanate, o-chlorophenyl isocyanate, p-methoxyphenyl isocyanate, m-ethoxyphenyl isocyanate, p-butoxyphenyl isocyanate, m-methoxyphenyl isocyanate, benzyl isocyanate, 1-phenylethyl isocyanate, 2-phenylethyl isocyanate, ethoxycarbonylmethyl isocyanate and methoxycarbonylmethyl isocyanate, respectively, reacts with 2-phenylbut-1-ene-2-sulfonamide, 2-(p-chlorophenyl)propene-1-sulfonamide, 2-(p-methoxyphenyl)propene-1-sulfonamide, 1-(m-chlorophenyl)propene-2-sulfonamide, 2-(p-chlorophenyl)-but-1-ene-1-sulfonamide, 1,2-diphenylethenesulfonamide, 3-phenylbut-2-ene-2-sulfonamide, 1-(p-chlorophenyl)propene-2-sulfonamide, 1-phenylpropene-2-sulfonamide, 1,2-diphenylpropene-1-sulfonamide, 1-(p-chlorophenyl)propene-2-sulfonamide, 2-(p-tolyl)-propene-1-sulfonamide, 2-(p-isopropylphenyl)propene-1-sulfonamide, 1-(p-ethoxyphenyl)propene-2-sulfonamide, 2-phenylpropene-1-sulfonamide, 2-(p-fluorophenyl)propene-1-sulfonamide, 2,2-diphenylethenesulfonamide, 2-(p-butoxyphenyl)propene-1-sulfonamide, 2-(p-tolyl)propene-1-sulfonamide, 1-phenylbut-1-ene-2-sulfonamide, 3(m-chlorophenyl)-but-2-ene-2-sulfonamide, 2-(p-chlorophenyl)-2-phenylethenesulfonamide, 2-(p-chlorophenyl)propene-1-sulfonamide, 2-(p-n-butylphenyl)propene-1-sulfonamide, 2-phenylpropene-1-sulfonamide, 1-phenylpropene-2-sulfonamide, 2-(m-methoxyphenyl)propene-1-sulfonamide and 2-(p-biphenylyl)propene-1-sulfonamide, respectively, according to the procedure of Example I, the following compounds are produced:

N-(N-methylcarbamoyl)-2-phenylbut-1-ene-1-sulfonamide,
N-(N-ethylcarbamoyl)-2-(p-chlorophenyl)propene-1-sulfonamide,
N-(N-isobutylcarbamoyl)-2-(p-methoxyphenyl)propene-1-sulfonamide,
N-(N-n-hexylcarbamoyl)-1(m-chlorophenyl)propene-2-sulfonamide,
N-(N-n-heptylcarbamoyl)-2-(p-chlorophenyl)but-1-ene-1-sulfonamide,
N-(N-decylcarbamoyl)-1,2-diphenylethenesulfonamide,
N-N-allylcarbamoyl)-2-phenylbut-2-ene-2-sulfonamide,
N-(N-[3,3-dimethylbut-2-yl]carbamoyl)-1-(p-chlorophenyl)propene-2-sulfonamide,
N-(N-cyclopropylcarbamoyl)-1-phenylpropene-2-sulfonamide,
N-(N-cyclopentylcarbamoyl)-1,2-diphenylpropene-1-sulfonamide,
N-(N-cyclohexylcarbamoyl)-1(p-chlorophenyl)propene-2-sulfonamide,
N-(N-cycloheptylcarbamoyl)-2-(p-tolyl)propene-1-sulfonamide,
N-(N-phenylcarbamoyl)-2-(p-isopropylphenyl)propene-1-sulfonamide,
N-(N-p-fluorophenylcarbamoyl)-1-(p-ethoxyphenyl)propene-2-sulfonamide,
N-(N-m-bromophenylcarbamoyl)-2-phenylpropene-1-sulfonamide,
N-(N-m-nitrophenylcarbamoyl)-2-(p-fluorophenyl)-propene-1-sulfonamide,
N-(N-p-tolylcarbamoyl)-2,2-diphenylethenesulfonamide,
N-(N-p-ethylphenylcarbamoyl)-2-(p-butoxyphenyl)-propene-1-sulfonamide,
N-(N-p-chlorophenylcarbamoyl)-2-(p-tolyl)propene-1-sulfonamide,
N-(N-p-chlorophenylcarbamoyl)-1-phenylbut-1-ene-2-sulfonamide,
N-(N-p-methoxyphenylcarbamoyl)-3-(m-chlorophenyl)but-2-ene-2-sulfonamide,
N-(N-m-ethoxyphenylcarbamoyl)-2-(p-chlorophenyl)-2-phenylethenesulfonamide,
N-(N-p-butoxyphenylcarbamoyl)-2-(p-chlorophenyl)propene-1-sulfonamide,
N-(N-m-methoxyphenylcarbamoyl)-2-(p-n-butylphenyl)propene-1-sulfonamide, N-(N-benzylcarbamoyl)-2-phenylpropene-1-sulfonamide,
N-(N-[1-phenylethyl]carbamoyl)-2-phenylpropene-1-sulfonamide,
N-(N-[2-phenylethyl]carbamoyl)-1-phenylpropene-2-sulfonamide,
N-(N-[ethoxycarbonylmethyl]carbamoyl)-2-(m-methoxyphenyl)propene-1-sulfonamide and
N-(N-[methoxycarbonylmethyl]carbamoyl)-2-(p-biphenylyl)propene-1-sulfonamide, respectively,

EXAMPLE IV

N-(N,N-Diphenylcarbamoyl)-2-phenylethenesulfonamide

To a suspension of 35g. of potassium carbonate in 500 ml. of acetone is added 18.3g. of 2-phenylethenesulfonamide and 35g. of N,N-diphenylcarbamoyl chloride. The reaction mixture is heated under reflux with stirring for 5½ hours. The insoluble materials are filtered from the hot acetone, and then the acetone is concentrated to dryness in vacuo. The residue is slurried in 300 ml. of ether and then filtered off. This gives 43g. of the potassium salt of the product.

The potassium salt is dissolved in a mixture of 200ml. of acetone and 50 ml. of water. The solution is acidified using concentrated hydrochloric acid, and then a further 50ml. of water is added. The solid which precipitates is filtered off, and washed successively with acetone-water (1:1) and then with water. This gives 33g. (87%) of N-(N,N-diphenylcarbamoyl)-2-phenylethenesulfonamide, m.p. 185°–188°C. Recrystallization of the product raises the melting point to 189°–191°C.

Analysis—Calcd. for $C_{21}H_{18}N_2O_3S$ (percent): C, 66.66; H, 4.80; N, 7.40. Found (percent): C, 66.46; H, 4.82; N, 7.17.

EXAMPLE V

When the procedure of Example IV is repeated, except that the N,N-diphenylcarbamoyl chloride used therein is replaced by an equimolar amount of N,N-dimethylcarbamoyl chloride, there is produced N-(N,N-dimethylcarbamoyl)-2-phenylethenesulfonamide, m.p. 160°–162° C.

Analysis — Calc'd for $C_{11}H_{14}N_2O_3S$ (percent): C, 51.96; H, 5.55, N, 11.02. Found (percent): C, 51.88; H, 5.56, N, 11.07.

EXAMPLE VI

The procedure of Example IV is repeated, except that the 2-phenyl ethenesulfonamide used therein is replaced by an equimolar amount of 1-phenylpropene-2-sulfonamide. The product is N-(N,N-diphenylcarbamoyl)-1-phenylpropene-2-sulfonamide, m.p. 175°–179° C.

Analysis — Calc'd for $C_{22}H_{20}N_2O_3S$ (percent): C, 67.33; H, 5.14, N, 7.14. Found (percent): C, 67.09; H, 5.24, N, 7.11.

EXAMPLE VII

When the procedure of Example IV is repeated, and the 2-phenylethenesulfonamide used therein is replaced by an equimolar amount of:
2-(4-biphenyl)ethenesulfonamide,
2-phenylpropene-1-sulfonamide,
2,2-diphenylethenesulfonamide,
1,2-diphenylethenesulfonamide,
2-phenylbut-1-ene-1-sulfonamide,
1-phenylbut-1-ene-2-sulfonamide,
3-phenylbut-2-ene-2-sulfonamide,
2-(m-chlorophenyl)ethenesulfonamide,
2-(o-chlorophenyl)ethenesulfonamide,
2-(p-chlorophenyl)ethenesulfonamide,
2-(p-bromophenyl)ethenesulfonamide,
2-(m-bromophenyl)ethenesulfonamide,
2-(p-fluorophenyl)ethenesulfonamide,
2-(m-tolyl)ethenesulfonamide,
2-(p-ethylphenyl)ethenesulfonamide,
2-(p-tert-butylphenyl)ethenesulfonamide,
2-(o-methoxyphenyl)ethenesulfonamide,
2-(m-isopropoxyphenyl)ethenesulfonamide,
2-(p-butoxyphenyl)ethenesulfonamide,
2-(m-chlorophenyl)propene-1-sulfonamide,
2-(p-chlorophenyl)propene-1-sulfonamide,
2-(m-bromophenyl)propene-1-sulfonamide,
2-(p-fluorophenyl)propene-1-sulfonamide,
2-(m-tolyl)propene-1-sulfonamide,
2-(p-isopropylphenyl)propene-1-sulfonamide,
2-(p-methoxyphenyl)propene-1-sulfonamide,
1-(o-chlorophenyl)propene-2-sulfonamide,
1-(m-chlorophenyl)propene-2-sulfonamide,
1-(p-chlorophenyl)propene-2-sulfonamide,
1-(p-fluorophenyl)propene- 2-sulfonamide,
1-(p-tolyl)propene-2-sulfonamide,
1-(m-methoxyphenyl)propene-2-sulfonamide,
1-(p-ethoxyphenyl)propene-2-sulfonamide,
2-(p-chlorophenyl)but-1-ene-1-sulfonamide,
2-(p-tolyl)but-1-ene-1-sulfonamide,
2-(m-methoxyphenyl)but-1-ene-1-sulfonamide,
1-(p-chlorophenyl)but-1-ene-2-sulfonamide,
1-(m-methoxyphenyl)but-1-ene-2-sulfonamide,
3-(p-chlorophenyl)but-2-ene-2-sulfonamide and
1,2-diphenylpropene-1-sulfonamide,
respectively, this affords:
N-(N,N-diphenylcarbamoyl)-2-(4-biphenyl)ethenesulfonamide,
N-(N,N-diphenylcarbamoyl)-2-phenylpropene-1-sulfonamide,
N-(N,N-diphenylcarbamoyl)-2,2-diphenylethenesulfonamide,
N-(N,N-diphenylcarbamoyl)1,2-diphenylethenesulfonamide,
N-(N,N-diphenylcarbamoyl)-2-phenylbut-1-ene-1-sulfonamide,
N-(N,N-diphenylcarbamoyl)-1-phenylbut-1-ene-2-sulfonamide,
N-(N,N-diphenylcarbamoyl)-3-phenylbut-2-ene-2-sulfonamide,
N-(N,N-diphenylcarbamoyl)-2-(m-chlorophenyl)ethenesulfonamide,
N-(N,N-diphenylcarbamoyl)-2-(o-chlorophenyl)ethenesulfonamide,
N-(N,N-diphenylcarbamoyl)-2-(p-chlorophenyl)ethenesulfonamide,
N-(N,N-diphenylcarbamoyl)-2-(p-bromophenyl)ethenesulfonamide,
N-(N,N-diphenylcarbamoyl)-2-(m-bromophenyl)ethenesulfonamide,
N-(N,N-diphenylcarbamoyl)-2-(p-fluorophenyl)ethenesulfonamide,
N-(N,N-diphenylcarbamoyl)-2-(m-tolyl)ethenesulfonamide,
N-(N,N-diphenylcarbamoyl)-2-(p-ethylphenyl)ethenesulfonamide,
N-(N,N-diphenylcarbamoyl)-2-(p-tert-butylphenyl)ethenesulfonamide, N-(N,N-diphenylcarbamoyl)-2-(o-methoxyphenyl)ethenesulfonamide,
N-(N,N-diphenylcarbamoyl)-2-(m-isopropoxyphenyl)ethenesulfonamide,
N-(N,N-diphenylcarbamoyl)-2-(p-butoxyphenyl)ethenesulfonamide,
N-(N,N-diphenylcarbamoyl)-2-(m-chlorophenyl)propene-1-sulfonamide,
N-(N,N-diphenylcarbamoyl)-2-(p-chlorophenyl)propene-1-sulfonamide,
N-(N,N-diphenylcarbamoyl)-2-(m-bromophenyl)propene-1-sulfonamide,
N-(N,N-diphenylcarbamoyl)-2-(p-fluorophenyl)propene-1-sulfonamide,
N-(N,N-diphenylcarbamoyl)-2-(m-tolyl)propene-1-sulfonamide,
N-(N,N-diphenylcarbamoyl)-2-(p-isopropylphenyl)propene-1-sulfonamide,
N-(N,N-diphenylcarbamoyl)-2-(p-methoxyphenyl)propene-1-sulfonamide,
N-(N,N-diphenylcarbamoyl)-1-(o-chlorophenyl)propene-2-sulfonamide,
N-(N,N-diphenylcarbamoyl)-1-(m-chlorophenyl)propene-2-sulfonamide,
N-(N,N-diphenylcarbamoyl)-1-(p-chlorophenyl)propene-2-sulfonamide,
N-(N,N-diphenylcarbamoyl)-1-(p-fluorophenyl)propene-2-sulfonamide,
N-(N,N-diphenylcarbamoyl)-1-(p-tolyl)propene-2-sulfonamide,
N-(N,N-diphenylcarbamoyl)-1-(m-methoxyphenyl)propene-2-sulfonamide,
N-(N,N-diphenylcarbamoyl)-1-(p-ethoxyphenyl)propene-2-sulfonamide,
N-(N,N-diphenylcarbamoyl)-2-(p-chlorophenyl)but-1-ene-1-sulfonamide,
N-(N,N-diphenylcarbamoyl)-2-(p-tolyl)but-1-ene-1-sulfonamide,
N-(N,N-diphenylcarbamoyl)-2-(m-methoxyphenyl)-but-1-ene-1-sulfonamide,
N-(N,N-diphenylcarbamoyl)-1-(p-chlorophenyl)but-1-ene-2-sulfonamide,
N-(N,N-diphenylcarbamoyl)-1-(m-methoxyphenyl)-but-1-ene-2-sulfonamide,
N-(N,N-diphenylcarbamoyl)-3-(p-chlorophenyl)but-2-ene-2-sulfonamide and
N-(N,N-diphenylcarbamoyl)-1,2-diphenylpropene-1-sulfonamide,
respectively.

EXAMPLE VIII

When the procedure of Example IV is repeated, and the alkenesulfonamide component is:
2-phenylethenesulfonamide,
1-phenylpropene-2-sulfonamide,
2-(p-methoxyphenyl)ethenesulfonamide,
2-(m-tolyl)ethenesulfonamide,
2-phenylethenesulfonamide,
1-(p-chlorophenyl)propene-2-sulfonamide,
1-(p-fluorophenyl)propene-2-sulfonamide,
3-phenylbut-2-ene-2-sulfonamide,
2-phenylethenesulfonamide,
2-(o-chlorophenyl)ethenesulfonamide,
2-(m-methoxyphenyl)propene-1-sulfonamide,
2-(p-tolyl)ethenesulfonamide,
2-(p-fluorophenyl)ethenesulfonamide,
2-phenylbut-1-ene-1-sulfonamide,
2-(p-chlorophenyl)ethenesulfonamide,
1-phenylbut-1-ene-2-sulfonamide,
2-(p-isopropoxyphenyl)ethenesulfonamide,
2-(m-chlorophenyl)ethenesulfonamide,
2-phenylethenesulfonamide,
2-(p-chlorophenyl)ethenesulfonamide,
1,2-diphenylethene and
2-phenylethenesulfonamide,
respectively, and the carbamoyl chloride component is:
N-phenyl-N-(p-chlorophenyl)carbamoyl chloride,
N-phenyl-N-(p-chlorophenyl)carbamoyl chloride,
N-phenyl-N-(p-chlorophenyl)carbamoyl chloride,
N-phenyl-N-(p-chlorophenyl)carbamoyl chloride,
N,N-di(p-methoxyphenyl)carbamoyl chloride,
N,N-di(p-methoxyphenyl)carbamoyl chloride,
N-methyl-N-(p-fluorophenyl)carbamoyl chloride,
N-methyl-N-(m-bromophenyl)carbamoyl chloride,
N-ethyl-N-(p-nitrophenyl)carbamoyl chloride,
N-(n-butyl)-N-(p-tolyl)carbamoyl chloride,
N-(n-decyl)-N-(p-ethylphenyl)carbamoyl chloride,
N-methyl-N-(p-tert-butylphenyl)carbamoyl chloride,
N-(n-propyl)-N-(m-isopropoxyphenyl)carbamoyl chloride,
N-(isopropyl)-N-(p-n-butoxyphenyl)carbamoyl chloride,
N-allyl-N-phenylcarbamoyl chloride,
N-benzyl-N-phenylcarbamoyl chloride,
piperidinocarbonyl chloride,
(4-benzylpiperidino)carbonyl chloride,
(4-[3-phenylprop-1-yl]piperidino)carbonyl chloride,
(4-[3-phenylprop-1-yl]piperidino)carbonyl chloride,
morpholinocarbonyl chloride and
(1,2,3,4-tetrahydroquinolino)carbonyl chloride,
respectively, the following compounds are prepared:
N-(N-phenyl-N-[p-chlorophenyl]carbamoyl)-2-phenylethenesulfonamide,
N-(N-phenyl-N-[p-chlorophenyl]carbamoyl)-1-phenylpropene-2-sulfonamide,
N-(N-phenyl-N-[p-chlorophenyl]carbamoyl)-2-(p-methoxyphenyl)ethenesulfonamide,
N-(N-phenyl-N-[p-chlorophenyl]carbamoyl)-2-(m-tolyl)ethenesulfonamide,
N-(N,N-di[p-methoxyphenyl]carbamoyl)-2-phenylethenesulfonamide,
N-(N,N-di[p-methoxyphenyl]carbamoyl)-1-(p-chlorophenyl)propene-2-sulfonamide,
N-(N-methyl-N-[p-fluorophenyl]carbamoyl)-1-(p-fluorophenyl)propene-2-sulfonamide,
N-(N-methyl-N-[m-bromophenyl]carbamoyl)-2-phenylbut-2-ene-2-sulfonamide,
N-(N-ethyl-N-[p-nitrophenyl]carbamoyl)-2-phenylethenesulfonamide,
N-(N-[n-butyl]-N-[p-tolyl]carbamoyl)-2-(o-chlorophenyl)ethenesulfonamide,
N-(N-[n-decyl]-N-[p-ethylphenyl]carbamoyl)-2-(m-methoxyphenyl)propene-1-sulfonamide,
N-(N-methyl-N-[p-tert-butylphenyl]carbamoyl)-2-(p-tolyl)ethenesulfonamide,
N-(N-[n-propyl]-N-[m-isopropoxyphenyl]carbamoyl)-2-(p-fluorophenyl)ethenesulfonamide,
N-(N-[isopropyl]-N-[p-n-butoxyphenyl]carbamoyl)-2-phenylbut-1-ene-1-sulfonamide,
N-(N-allyl-N-phenylcarbamoyl)-2-(p-chlorophenyl)ethenesulfonamide,
N-(N-benzyl-N-phenylcarbamoyl)-1-phenylbut-1-ene-2-sulfonamide,
N-(piperidinocarbonyl)-2-(p-isopropoxyphenyl)ethenesulfonamide, N-([4-benzylpiperidino]carbonyl)-2-(m-chloro-phenyl)ethenesulfonamide,
N-([4-(3-phenylprop-1-yl)piperidino]carbonyl)-2-phenylethenesulfonamide,
N-([4-(3-phenylprop-1-yl)piperidino]carbonyl)-2-(p-chlorophenylethenesulfonamide,
N-(morpholinocarbonyl)-1,2-diphenylethenesulfonamide and
N-([1,2,3,4-tetrahydroisoquinolino]carbonyl)-2-phenylethenesulfonamide,
respectively.

EXAMPLE IX

N-(N-[Bicyclo[2.2.1]hept-2-en-5-ylmethyl]carbamoyl)-2-phenylethenesulfonamide

To a solution of 1.8 g. of 2-phenylethenesulfonamide and 4.8 g. of 1,1-diphenyl-3-(bicyclo[2.2.1]hept-2-en-5-ylmethyl)urea in 20 ml. of N,N-dimethylformamide, is added, with stirring, 0.64 g. of a 56.6% dispersion of sodium hydride in mineral oil. The mixture is stirred at ambient temperature overnight, during which time a heavy precipitate forms. To the reaction mixture is then added 200 ml. of ether. After stirring for 15 minutes, the precipitate is filtered off. It is dissolved in 50 ml. of water, and then the crude product is precipitated by acidification using concentrated hydrochloric acid. It is filtered off and recrystallized from aqueous acetone. The yield is 1.9 g. (56%) of a solid, m.p. 161°–163.5° C.

Analysis — Calc'd for $C_{17}H_{20}N_2O_3S$ (percent): C, 61.43; H, 6.07; N, 9.43. Found (percent): C, 61.13; H, 5.95; N, 8.30.

When the above procedure is repeated, and the 2-phenylethenesulfonamide is replaced by an equimolar amount of 2-phenylpropene-1-sulfonamide, 1-phenylpropene-2-sulfonamide, 3-phenylbut-2-ene-2-sulfonamide, 1-phenylbut-1-ene-2-sulfonamide, 2,2-diphenylethenesulfonamide, 2-(p-chlorophenyl)ethenesulfonamide, 2-(m-tolyl)ethenesulfonamide, 2-(p-methoxyphenyl)ethenesulfonamide and 2-(p-chlorophenyl)propene-1-sulfonamide, respectively, there is produced:
N-(N-[bicyclo[2.2.1]hept-2-en-5-ylmethyl]carbamoyl)-2-phenylpropene-1-sulfonamide,
N-(N-[bicyclo[2.2.1]hept-2-en-5-ylmethyl]carbamoyl)-1-phenylpropene-1-sulfonamide,
N-(N-[bicyclo[2.2.1]hept-2-en-5-ylmethyl]carbamoyl)-3-phenylbut-2-ene-2-sulfonamide,
N-(N-[bicylco[2.2.1]hept-2-en-5-ylmethyl]carbamoyl)-1-phenylbut-1-ene-2-sulfonamide,
N-(N-[bicyclo[2.2.1]hept-2-en-5-ylmethyl]carbamoyl)-2,2-diphenylethenesulfonamide,
N-(N-[bicyclo[2.2.1]hept-2-en-5-ylmethyl]carbamoyl)-2-(p-chlorophenyl)ethenesulfonamide,
N-(N-[bicyclo[2.2.1]hept-2-en-5-ylmethyl]carbamoyl)-2-(m-tolyl)ethenesulfonamide,
N-(N-[bicyclo[2.2.1]hept-2-en-5-ylmethyl]carbamoyl)-2-(p-methoxyphenyl)ethenesulfonamide and
N-(N-[bicyclo[2.2.1]hept-2-en-5-ylmethyl]carbamoyl)-2-(p-chlorophenyl)propene-1-sulfonamide,
respectively.

EXAMPLE X

Following the procedure of Example IX, and using 2-phenylethenesulfonamide and 1,1-diphenyl-3-(endo-7-oxabicyclo[2.2.1]heptan-2-ylmethyl)urea as starting materials, is prepared N-(N-[endo-7-oxabicyclo[2.2.1]heptan-2-ylmethyl]carbamoyl)-2-phenylethenesulfonamide, m.p. 176°–178° C.

Analysis — Calc'd for $C_{16}H_{20}N_2O_4S$ (percent): C, 57.13; H, 5.99; N, 8.33. Found (percent): C, 56.83; H, 6.06; N, 8.24.

Again following the procedure of Example IX, and using 2-phenylethenesulfonamide and 1,1-diphenyl-3-(exo-7-oxabicyclo[2.2.1]haptan-2-ylmethyl)urea as starting materials, is prepared N-(N-[exo-7-oxabicyclo[2.2.1]heptan-2-ylmethyl]carbamoyl)-2-phenylethenesulfonamide, m.p. 150°–152° C.

Analysis — Calc'd for $C_{16}H_{20}N_2O_4S$ (percent): C, 57.13; H, 5.99; N, 8.33. Found (percent): C, 56.88; H, 6.04; N, 8.28.

Condensation of 1,1-diphenyl-3-(endo-7-oxabicyclo[2.2.1]heptan-2-ylmethyl)urea with 2-phenylpropene-1-sulfonamide, 3-phenylbut-2-ene-2-sulfonamide, 2,2-diphenylethenesulfonamide, 2-(m-chlorophenyl)ethenesulfonamide, 2-(m-methoxyphenyl)ethenesulfonamide and 2-(p-chlorophenyl)propene-1-sulfonamide, respectively, according to the procedure of Example VIII, produces:
N-(N-[endo-7-oxabicyclo[2.2.1]heptan-2-ylmethyl]carbamoyl)-2-phenylpropene-1-sulfonamide,
N-(N-[endo-7-oxabicyclo[2.2.1]heptan-2-ylmethyl]carbamoyl)-3-phenylbut-2-ene-2-sulfonamide,
N-(N-[endo-7-oxabicyclo[2.2.1]heptan-2-ylmethyl]carbamoyl)-2,2-diphenylethenesulfonamide,
N-(N-[endo-7-oxabicyclo[2.2.1]heptan-2-ylmethyl]carbamoyl)-2-(m-chlorophenyl)ethenesulfonamide,
N-(N-[endo-7-oxabicyclo[2.2.1]heptan-2-ylmethyl]carbamoyl)-2-(m-methoxyphenyl)ethenesulfonamide and
N-(N-[endo-7-oxabicyclo[2.2.1]heptan-2-ylmethyl]carbamoyl-2-(p-chlorophenyl)propene-1-sulfonamide,
respectively.

In like manner, condensation of 1,1-diphenyl-3-(exo-7-oxabicyclo[2.2.1]heptan-2-ylmethyl)urea with 1-phenylpropene-2-sulfonamide, 1-phenylbut-1-ene-2-sulfonamide, 2-(p-chlorophenyl)ethenesulfonamide, 2-(p-isopropylphenyl)ethenesulfonamide and 1-(p-chlorophenyl)propene-2-sulfonamide, respectively, according to the procedure of Example VIII, affords:
N-(N-[exo-7-oxabicyclo[2.2.1]heptan-2-ylmethyl]carbamoyl)-1-phenylpropene-2-sulfonamide,
N-(N-[exo-7-oxabicyclo[2.2.1]heptan-2-ylmethyl]carbamoyl)-1-phenylbut-1-ene-2-sulfonamide,
N-(N-[exo-7-oxabicyclo[2.2.1]heptan-]-ylmethyl]carbamoyl)-2-(p-chlorophenyl)ethenesulfonamide,
N-(N-[exo-7-oxabicyclo[2.2.1]heptan-2-ylmethyl]carbamoyl)-2-(p-isopropylphenyl)ethenesulfonamide, and
N-(N-[exo-7-oxabicyclo[2.2.1]heptan-2-ylmethyl]carbamoyl)-1-(p-chlorophenyl)propene-2-sulfonamide,
respectively.

EXAMPLE XI

N-(Piperidinocarbonyl)-1-phenylpropene-2-sulfonamide

A solution of 1.9g. of N-(N,N-diphenylcarbamoyl)-1-phenylpropene-2-sulfonamide and 1.7g of piperidine in 10ml. of N,N-dimethylformamide is maintained at ca. 95°C. for 6 hours. It is then cooled to ambient temperature, and 100 ml. of ether is added. The mixture is extracted with 50 ml. of water, and then the water extract is acidified using concentrated hydrochloric acid. This causes the crude product to precipitate. It is filtered off, and then it is recrystallized from a mixture of acetone and water giving 670 mg. of N-(piperidinocarbonyl)-1-phenylpropene-2-sulfonamide, m.p. 159°–161° C.

Analysis—Calcd. for $C_{15}H_{20}N_2O_3S$ (percent): C, 58.43; H, 6.54; N, 9.09. Found (percent): C, 58.21; H, 6.50; N, 9.05.

EXAMPLE XII

Following the procedure of Example XI, and reacting either N-(N,N-diphenylcarbamoyl)-1-phenylpropene-2-sulfonamide or N-(N,N-diphenylcarbamoyl)-2-phenylethenesulfonamide with the appropriate amine, the following compounds are prepared:

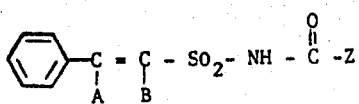

scribed in Examples IV, V and VII, with the appropriate amine, according to the procedure of Example XI, affords the following congeners:

N-(piperidinocarbonyl)-2-(4-biphenylyl)ethenesulfonamide,
N-(piperidinocarbonyl)-2-phenylpropene-1-sulfonamide,
N-(piperidinocarbonyl)-2,2-diphenylethenesulfonamide,
N-(piperidinocarbonyl)-1-phenylbut-1-ene-2-sulfonamide,
N-(piperidinocarbonyl)-2-(m-chlorophenyl)ethenesulfonamide,
N-(piperidinocarbonyl)-2-(p-methoxyphenyl)propene-1-sulfonamide,
N-([4-hydroxypiperidino]carbonyl)-2-(p-fluorophenyl)-propene-1-sulfonamide,
N-([4hydroxypiperidino]carbonyl)-2-(p-tert-butylphenyl)ethenesulfonamide,
N-([4-methoxypiperidino]carbonyl)-1-(p-chlorophenyl)propene-2-sulfonamide,
N-([4-methoxypiperidino]carbonyl)-2-(p-ethylphenyl)ethenesulfonamide,
N-([4-phenylpiperidino]carbonyl)-2-phenylpropene-1-sulfonamide,
N-([4-phenylpiperidino]carbonyl)-1-phenylpro-

|  |  |  |  | Analysis | | | | | |
|---|---|---|---|---|---|---|---|---|---|
|  |  |  |  | Calc'd (%) | | | Found (%) | | |
| A | B | Z | m.p. (°C.) | C | H | N | C | H | N |
| hydrogen | hydrogen | N-(bicyclo[2.2.1]heptan-2-yl-methyl)amino | 175–177 | 61.07 | 6.58 | 8.38 | 61.24 | 6.77 | 8.10 |
| hydrogen | hydrogen | N-methyl-N-(2-phenylethyl)-amino | 143–144.5 | 62.78 | 5.85 | 8.14 | 62.77 | 5.89 | 8.06 |
| hydrogen | hydrogen | 4-benzylpiperidino | 175–177 | 65.61 | 6.29 | 7.29 | 65.66 | 6.45 | 7.16 |
| hydrogen | hydrogen | 1,2,5,6-tetrahydropyridino | 170–172 | 57.53 | 5.52 | 9.59 | 57.55 | 5.58 | 9.56 |
| hydrogen | hydrogen | 4-propylpiperidino | 146–148 | 60.70 | 7.19 | 8.33 | 60.48 | 8.67 | 8.17 |
| hydrogen | hydrogen | 2-ethylpiperidino | 138–140 | 59.61 | 6.88 | 8.69 | 59.51 | 6.85 | 8.65 |
| hydrogen | hydrogen | N-(azacycloheptan-1-yl)amino | 128–129 | 58.43 | 6.54 | 9.09 | 58.20 | 6.51 | 9.04 |
| hydrogen | hydrogen | 2-(2-hydroxyethyl)piperidino | 180–181.5 | 56.79 | 6.55 | 8.28 | 56.38 | 6.49 | 8.25 |
| hydrogen | hydrogen | 2-methylpiperidino | 138–140 | 58.43 | 6.54 | 9.09 | 58.00 | 6.46 | 9.32 |
| hydrogen | hydrogen | N,N-di(2-methylprop-1-yl)-amino | 157.5–158.5 | 60.34 | 7.74 | 8.28 | 60.17 | 7.68 | 8.29 |
| hydrogen | hydrogen | N,N-diisopropylamino | 168–169 | 58.00 | 7.15 | 9.03 | 57.60 | 7.08 | 8.91 |
| hydrogen | hydrogen | N-(azacyclooctan-1-yl)amino | 107–109 | 59.61 | 6.88 | 8.69 | 59.45 | 6.79 | 8.68 |
| hydrogen | hydrogen | thiomorpholino | 163–166 | 50.00 | 5.16 | 8.97 | 49.95 | 5.25 | 8.99 |
| hydrogen | hydrogen | 3,5-dimethylpiperidino | 149–151 | 59.61 | 6.88 | 8.69 | 59.64 | 6.88 | 8.56 |
| hydrogen | hydrogen | N-benzyl-N-ethylamino | 79–80 | 62.78 | 5.85 | 8.14 | 62.66 | 5.82 | 8.13 |
| hydrogen | hydrogen | 4-methylpiperidino | 169–171 | 58.43 | 6.54 | 9.09 | 58.09 | 6.40 | 9.07 |
| hydrogen | methyl | piperidino | 159–161 | 58.43 | 6.54 | 9.09 | 58.21 | 6.50 | 9.05 |
| hydrogen | hydrogen | N,N-di(ethoxycarbonylmethyl)-amino | 112–114 | 51.25 | 5.57 | 7.03 | 51.10 | 5.60 | 7.02 |
| hydrogen | methyl | 1,2,3,4-tetrahydroisoquinolino | 147–148.5 | 64.03 | 5.66 | 7.86 | 64.01 | 5.67 | 7.89 |
| hydrogen | methyl | pyrrolidino | 151–153 | 57.13 | 6.17 | 9.52 | 56.92 | 6.09 | 9.47 |
| hydrogen | methyl | morpholino | 145–147 | 54.19 | 5.85 | 9.03 | 54.14 | 5.89 | 8.98 |
| hydrogen | methyl | N,N-diethylamino | 122–124 | 56.73 | 6.74 | 9.45 | 56.39 | 6.80 | 9.38 |
| hydrogen | hydrogen | 4-phenylpiperidino | 135–137 | 64.78 | 5.98 | 7.56 | 64.90 | 6.28 | 7.41 |
| hydrogen | hydrogen | 4-(3-phenylpropyl)piperidino | 131.5–133 | 66.97 | 6.84 | 6.79 | 66.68 | 7.11 | 6.92 |
| hydrogen | hydrogen | 4-methoxypiperidino | 154.5–156.5 | 55.55 | 6.22 | 8.64 | 55.59 | 6.22 | 8.54 |
| hydrogen | hydrogen | N,N-didecylamino* | 154–157 | 65.87 | 9.34 | 5.30 | 66.11 | 9.12 | 5.29 |
| hydrogen | hydrogen | N-(ethoxycarbonylmethyl)-N-benzylamino | 130–133 | 59.69 | 5.51 | 6.96 | 59.54 | 5.53 | 6.89 |
| hydrogen | hydrogen | N-(ethoxycarbonylmethyl)-N-methylamino | 126–128 | 51.51 | 5.56 | 8.58 | 51.62 | 5.50 | 8.46 |
| hydrogen | methyl | 4-(3-phenylpropyl)piperidino | 129–131 | 67.57 | 7.08 | 6.56 | 67.70 | 7.22 | 6.32 |
| hydrogen | hydrogen | 3,4-dichloropiperidino | 195–197 | 46.27 | 4.44 | 7.71 | 46.32 | 4.39 | 7.61 |
| hydrogen | hydrogen | 4-(3-[4-methoxyphenyl]propyl)-piperidino* | 214–216 | 62.09 | 6.25 | 6.03 | 62.13 | 6.46 | 5.99 |
| hydrogen | hydrogen | morpholino | 174–176 |  |  |  |  |  |  |
| hydrogen | hydrogen | 1,2,3,4-tetrahydroisoquinolino | 165–167 |  |  |  |  |  |  |
| hydrogen | hydrogen | pyrrolidino | 199 |  |  |  |  |  |  |
| hydrogen | hydrogen | N,N-diethylamino | 113–115 |  |  |  |  |  |  |

*This compound is isolated, and analyzed, as its sodium salt.

EXAMPLE XIII

Reaction of the appropriate N-(N,N-diphenylcarbamoyl)alkenesulfonamide, selected from those described in Examples IV, V and VII, with the appropriate amine, according to the procedure of Example XI, affords the following congeners:

pene-2-sulfonamide,
N-([4-phenylpiperidino]carbonyl)-2,2-diphenylethenesulfonamide, N-([4-phenylpiperidino]carbonyl)-2-(p-chlorophenyl)ethenesulfonamide,
N-([4-phenylpiperidino]carbonyl)-2-(p-tolyl)but-1-ene-1-sulfonamide,
N-([4-propylpiperidino]carbonyl)-1-phenylpropene-2-sulfonamide,
N-([4-methylpiperidino]carbonyl)-2-(m-bromophenyl)propene-1-sulfonamide,
N-([2-methylpiperidino]carbonyl)-2,2-diphenylethenesulfonamide,
N-([3-methylpiperidino]carbonyl)-2-(p-butoxyphenyl)ethenesulfonamide,
N-([2-ethylpiperidino]carbonyl)-1-(p-chlorophenyl)propene-2-sulfonamide,
N-([2-ethylpiperidino]carbonyl)-2-(m-methoxyphenyl)but-1-ene-1-sulfonamide,
N-([4-benzylpiperidino]carbonyl)-2-phenylpropene-1-sulfonamide,
N-([4-benzylpiperidino]carbonyl)-1-(p-chlorophenyl)propene-2-sulfonamide,
N-([4-benzylpiperidino]carbonyl)-2-(m-bromophenyl)ethenesulfonamide,
N-([4-benzylpiperidino]carbonyl)-2-(p-fluorophenyl)ethenesulfonamide,
N-([4-benzylpiperidino]carbonyl)-1-(p-ethoxyphenyl)propene-2-sulfonamide,
N-([4-benzylpiperidino]carbonyl)-2-(p-tolyl)but-1-ene-1-sulfonamide,
N-([4-(2-phenylethyl)piperidino]carbonyl)-2-phenylethenesulfonamide,
N-([4-(2-phenylethyl)piperidino]carbonyl)-2-(p-chlorophenyl)ethenesulfonamide,
N-([4-(2-phenylethyl)piperidino]carbonyl)-2-(p-isopropylphenyl)propene-1-sulfonamide,
N-([4-(2-phenylethyl)piperidino]carbonyl)-2-(m-isopropoxyphenyl)ethenesulfonamide,
N-([4-(2-phenylethyl)piperidino]carbonyl)-2-(p-fluorophenyl)ethenesulfonamide,
N-(azacycloheptan-1-ylcarbonyl)-1-phenylpropene-2-sulfonamide,
N-(azacycloheptan-1-ylcarbonyl)-2-(o-chlorophenyl)ethenesulfonamide,
N-(azacycloheptan-1-ylcarbonyl)-3-phenylbut-2-ene-2-sulfonamide,
N-(pyrrolidinocarbonyl)-2-(m-chlorophenyl)ethenesulfonamide,
N-(pyrrolidinocarbonyl)-2-(m-tolyl)ethenesulfonamide,
N-(morpholinocarbonyl)-1-phenylbut-1-ene-2-sulfonamide,
N-(morpholinocarbonyl)-2-(p-chlorophenyl)propene-1-sulfonamide,
N-(morpholinocarbonyl)-2-(m-isopropoxyphenyl)ethenesulfonamide,
N-(morpholinocarbonyl)-(p-isopropylphenyl)propene-1-sulfonamide,
N-(morpholinocarbonyl)-2,2-diphenylethenesulfonamide,
N-(morpholinocarbonyl)-1,2-diphenylpropene-1-sulfonamide,
N-(thiomorpholinocarbonyl)-2-(p-bromophenyl)ethenesulfonamide,
N-(thiomorpholinocarbonyl)-2-(p-fluorophenyl)propene-1-sulfonamide,
N-(1,2,3,4-tetrahydroisoquinolinocarbonyl)-2-phenylpropene-1-sulfonamide,
N-(1,2,3,4-tetrahydroisoquinolinocarbonyl)-2-phenylbut-1-ene-1-sulfonamide,
N-(1,2,3,4-tetrahydroisoquinolinocarbonyl)-2-(m-chlorophenyl)ethenesulfonamide,
N-(1,2,3,4-tetrahydroisoquinolinocarbonyl)-2-(p-bromophenyl)ethenesulfonamide,
N-(1,2,3,4-tetrahydroisoquinolinocarbonyl)-2-(p-tert-butylphenyl)ethenesulfonamide,
N-(1,2,3,4-tetrahydroisoquinolinocarbonyl)-2-(p-fluorophenyl)propene-1-sulfonamide,
N-(1,2,3,4-tetrahydroisoquinolinocarbonyl)-2-(m-methoxyphenyl)but-1-ene-1-sulfonamide,
N-(1,2,3,4-tetrahydroisoquinolinocarbonyl)-2-(p-chlorophenyl)ethenesulfonamide,
N-(N,N-dimethylcarbamoyl)-2-(p-chlorophenyl)ethenesulfonamide,
N-(N,N-diethylcarbamoyl)-2-(m-tolyl)propene-1-sulfonamide,
N-(N,N-diisopropylcarbamoyl)-2-(m-isopropoxyphenyl)ethenesulfonamide,
N-(N,N-diallylcarbamoyl)-1-phenylpropene-2-sulfonamide,
N-(N,N-diallylcarbamoyl)-2-(p-chlorophenyl)propene-1-sulfonamide,
N-(N-[2-methylallyl]carbamoyl)-1-(p-tolyl)propene-2-sulfonamide,
N-(N-[4-methylpent-3-enyl]carbamoyl)-1-(m-methoxyphenyl)but-1-ene-2-sulfonamide,
N-(N-methyl-N-allylcarbamoyl)-2-(p-fluorophenyl)ethenesulfonamide,
N-(N-methyl-N-cyclohexyl)-2-phenylethenesulfonamide,
N-(N,N-dicyclohexylcarbamoyl)-3-(p-chlorophenyl)but-2-ene-2-sulfonamide,
N-(N-[2-phenylethyl]carbamoyl)-1-phenylpropene-2-sulfonamide,
N-(N-methyl-N-[2-phenylethyl]carbamoyl)-2-(p-chlorophenyl)ethenesulfonamide,
N-(4-[4-phenylbutyl]piperidinocarbonyl)-2-phenylethenesulfonamide,
N-(4-[5-phenylpentyl]piperidinocarbonyl)-2-phenylethenesulfonamide,
N-(3-[3-phenylpropyl]piperidinocarbonyl)-2-phenylethenesulfonamide,
N-(2-[3-phenylpropyl]piperidinocarbonyl)-2-phenylethenesulfonamide,
N-(4-[2-(p-isopropoxyphenyl)ethyl]piperidinocarbonyl)-2-(p-chlorophenyl)ethenesulfonamide,
N-(3-[3-(p-butoxyphenyl)propyl]piperidinocarbonyl)-2-(o-tolyl)ethenesulfonamide,
N-(3-[3-(p-isopropylphenyl)propyl]piperidinocarbonyl)-2-phenylpropene-1-sulfonamide,
N-(4-[3-(p-t-butylphenyl)propyl]piperidinocarbonyl)-1-phenylpropene-2-sulfonamide,
N-(4-[m-methylbenzyl]piperidinocarbonyl)-2-phenylethenesulfonamide,
N-(4-[3-(m-methoxyphenyl)propyl]piperidinocarbonyl)-2-phenylethenesulfonamide,
N-(4-[3-(o-methoxyphenyl)propyl]piperidinocarbonyl)-2-phenylethenesulfonamide,
N-(4-[2-(p-methoxyphenyl)ethyl]piperidinocarbonyl)-2-(p-chlorophenyl)ethenesulfonamide,
N-(4-[4-(m-methoxyphenyl)butyl]piperidinocarbonyl)-1-(p-tolyl)propene-2-sulfonamide,
N-(4-[2-phenylprop-1-yl]piperidinocarbonyl)-2-phenylethenesulfonamide, and
N-(4-[2-phenylbut-1-yl]piperidinocarbonyl)-2-(p-chlorophenyl)ethenesulfonamide,
respectively.

EXAMPLE XIV

The procedure of Example XI is repeated, except that the piperidine used therein is replaced by an equimolar amount of 4-(3-phenylpropyl)piperidine, and the N-(N,N-diphenylcarbamoyl)-1-phenylpropene-2-sulfonamide used therein is replaced by:

N-(N-phenyl-N-[p-chlorophenyl]carbamoyl)-2-phenylethenesulfonamide,
N-(N-phenyl-N-[p-chlorophenyl]carbamoyl)-2-(p-methoxyphenyl)ethenesulfonamide,
N-(N,N-di[p-methoxyphenyl]carbamoyl)-1-(p-chlorophenyl)propene-2-sulfonamide,
N-(N-[n-butyl]-N-[p-tolyl]carbamoyl)-2-(o-chlorophenyl)ethenesulfonamide,
N-(N-methyl-N-[p-tert-butylphenyl]carbamoyl)-2-(p-tolyl)ethenesulfonamide,
N-(N-[n-propyl]-N-[m-isopropoxyphenyl]carbamoyl)-2-(p-fluorophenyl)ethenesulfonamide and
N-(N-benzyl-N-phenylcarbamoyl)-1-phenylbut-1-ene-2-sulfonamide, respectively.

This affords:

N-([4-(3-phenylpropyl)piperidino]carbonyl)-2-phenylethenesulfonamide,
N-([4-(3-phenylpropyl)piperidino]carbonyl)-2-(p-methoxyphenyl)ethenesulfonamide,
N-([4-(3-phenylpropyl)piperidino]carbonyl)-1-(p-chlorophenyl)propene-2-sulfonamide,
N-([4-(3-phenylpropyl)piperidino]carbonyl)-2-(o-chlorophenyl)ethenesulfonamide,
N-([4-(3-phenylpropyl)piperidino]carbonyl)-2-(p-tolyl)ethenesulfonamide,
N-([4-(3-phenylpropyl)piperidino]carbonyl)-2-(p-fluorophenyl)ethenesulfonamide and
N-([4-(3-phenylpropyl)piperidino]carbonyl)-1-phenylbut-1-ene-2-sulfonamide, respectively.

EXAMPLE XV

N-(N-[1-Methoxycarbonylethyl]carbamoyl)-2-phenylethenesulfonamide

To a solution of 3.5 g. of DL-alanine methyl ester hydrochloride in 20 ml. of N,N-dimethylformamide is added 1.05 g. of a 56.6% suspension of sodium hydride in mineral oil. The mixture is stirred at ambient temperature for 15 minutes, and then 3.8 g. of N-(N,N-diphenylcarbamoyl)-2-phenylethenesulfonamide is added. The whole reaction mixture is then maintained at ca. 90° C. for 40 minutes. After being allowed to cool to room temperature, it is diluted with an excess of ether and then it is extracted with water. Acidification of the water extract with dilute hydrochloric acid causes precipitation of the crude product, which is then filtered off. The ether phase is washed with dilute hydrochloric acid, which causes a further crop of product to precipitate. It is filtered off and the two crops of product are combined. This yields 1.55 g. of material having a melting point of 135°–139° C. The crude product is recrystallized from a mixture of acetone and hexane, giving 0.70 g. of N-[N-(1-methoxycarbonylethyl)carbamoyl]-2-phenylethenesulfonamide, m.p. 138°–140° C.

Analysis — Calc'd for $C_{13}H_{16}N_2O_5S$ (percent): C, 49.94; H, 5.12; N, 8.96. Found (percent): C, 50.06; H, 5.26; N, 9.32.

EXAMPLE XVI

Following the procedure of Example XIV, and replacing the DL-alanine methyl ester hydrochloride used therein by the appropriate amino-ester hydrochloride, the following compounds are prepared.

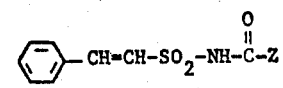

| Z | M.P. (°C.) | Calc'd (%) C | H | N | Found (%) C | H | N |
|---|---|---|---|---|---|---|---|
| N-(1-ethoxycarbonyl-2-methylprop-1-yl)-amino | 127–129 | 54.23 | 6.26 | 7.91 | 54.23 | 6.29 | 7.93 |
| N-(1-ethoxycarbonyl-2-methylbut-1-yl-amino | 126–128 | 55.43 | 6.56 | 7.61 | 55.52 | 6.54 | 7.48 |
| N-(1-ethoxycarbonyl-pent-1-yl)amino | 81–83 | 55.43 | 6.56 | 7.61 | 55.25 | 6.49 | 7.77 |
| N-(5-ethoxycarbonyl-pent-1-yl)amino | 97–99 | 55.43 | 6.56 | 7.61 | 55.50 | 6.56 | 7.65 |
| N-(1,3-dimethoxycarbonylprop-1-yl)amino | 120–122 | 50.00 | 5.25 | 7.29 | 49.89 | 5.22 | 7.11 |
| N-(1-ethoxycarbonyl-prop-1-yl)amino | 149–151 | 52.92 | 5.92 | 8.23 | 52.69 | 5.89 | 8.23 |
| N-(3-ethoxycarbonyl-prop-1-yl)amino | 120–122 | 52.92 | 5.92 | 8.23 | 52.76 | 5.90 | 8.28 |

EXAMPLE XVII

When the procedure of Example XV is repeated, and the alkenesulfonamide component is:

1-phenylpropene-2-sulfonamide,
2-phenylpropene-1-sulfonamide,
2-(p-chlorophenyl)ethenesulfonamide,
1,1-diphenylethenesulfonamide,
2-(p-tolyl)ethenesulfonamide,
1-phenylpropene-2-sulfonamide,
2-phenylpropene-1-sulfonamide,
2-(m-chlorophenyl)ethenesulfonamide,
2-(p-bromophenyl)ethenesulfonamide,
1-(m-methoxyphenyl)propene-2-sulfonamide,
2-(p-fluorophenyl)ethenesulfonamide,
3-phenylbut-2-ene-2-sulfonamide,
2-phenylbut-1-ene-1-sulfonamide,
2-(p-chlorophenyl)propene-1-sulfonamide,
2-(p-isopropylphenyl)propene-1-sulfonamide,
2-phenylpropene-1-sulfonamide,
2-(o-chlorophenyl)ethenesulfonamide, 1-phenylbut-1-ene-2-sulfonamide,
1,2-diphenylethenesulfonamide,
2-phenylethenesulfonamide,
1-(m-chlorophenyl)propene-2-sulfonamide,
2-(m-tolyl)ethenesulfonamide and
2-(p-isopropoxyphenyl)ethenesulfonamide,
respectively, and the amino-acid ester hydrochloride component is the hydrochloride salt of:
glycine methyl ester,
glycine methyl ester,
glycine methyl ester,
glycine methyl ester,
glycine methyl ester,
glycine ethyl ester,
glycine ethyl ester,
glycine ethyl ester,
glycine ethyl ester,
glycine ethyl ester,
DL-alanine methyl ester,
DL-alanine methyl ester,
DL-alanine methyl ester,
DL-alanine methyl ester,
DL-alanine methyl ester,
DL-leucine ethyl ester,
DL-leucine ethyl ester,
DL-leucine ethyl ester,
DL-leucine ethyl ester,
ω-aminooctanoic acid ethyl ester,
ω-aminooctanoic acid ethyl ester,
ω-aminooctanoic acid ethyl ester and
ω-aminooctanoic acid ethyl ester,
respectively, there is produced:
N-(N-[methoxycarbonylmethyl]carbamoyl)-1-phenylpropene-2-sulfonamide,
N-(N-[methoxycarbonylmethyl]carbamoyl)-2-phenylpropene-1-sulfonamide,
N-(N-[methoxycarbonylmethyl]carbamoyl)-2-(p-chlorophenyl)ethenesulfonamide,
N-(N-[methoxycarbonylmethyl]carbamoyl)-1,1-diphenylethenesulfonamide,
N-(N-[methoxycarbonylmethyl]carbamoyl)-2-(p-tolyl)-ethenesulfonamide,
N-(N-[ethoxycarbonylmethyl]carbamoyl)-1-phenylpropene-2-sulfonamide,
N-(N-[ethoxycarbonylmethyl]carbamoyl)-2-phenylpropene-1-sulfonamide,
N-(N-[ethoxycarbonylmethyl]carbamoyl)-2-(m-chlorophenyl)ethenesulfonamide,
N-(N-[ethoxycarbonylmethyl]carbamoyl)-2-(p-bromophenyl)ethenesulfonamide,
N-(N-[ethoxycarbonylmethyl]carbamoyl)-1-(m-methoxyphenyl)propene-2-sulfonamide,
N-(N-[1-methoxycarbonylethyl]carbamoyl)-2-(p-fluorophenyl)ethenesulfonamide,
N-(N-[1-methoxycarbonylethyl]carbamoyl)-3-phenylbut-2-ene-2-sulfonamide,
N-(N-[1-methoxycarbonylethyl]carbamoyl)-2-phenylbut-1-ene-1-sulfonamide,
N-(N-[1-methoxycarbonylethyl]carbamoyl)-2-(p-chlorophenyl)propene-1-sulfonamide,
N-(N-[1-methoxycarbonylethyl]carbamoyl)-2-(p-isopropylphenyl)propene-1-sulfonamide,
N-(N-[1-ethoxycarbonyl-2-methylbut-1-yl]carbamoyl)-2-phenylpropene-1-sulfonamide,
N-(N-[1-ethoxycarbonyl-2-methylbut-1-yl]carbamoyl)-2-(o-chlorophenyl)ethenesulfonamide,
N-(N-[1-ethoxycarbonyl-2-methylbut-1-yl]carbamoyl)-1-phenylbut-1-ene-2-sulfonamide,
N-(N-[1-ethoxycarbonyl-2-methylbut-1-yl]carbamoyl)-1,2-diphenylethenesulfonamide,
N-(N-[7-ethoxycarbonylhept-1-yl]carbamoyl)-2-phenylethenesulfonamide,
N-(N-[7-ethoxycarbonylhept-1-yl]carbamoyl)-1-(m-chlorophenyl)propene-2-sulfonamide,
N-(N-[7-ethoxycarbonylhept-1-yl]carbamoyl)-2-(m-tolyl)ethenesulfonamide and
N-(N-[7-ethoxycarbonylhept-1-yl]carbamoyl)-2-(p-isopropoxyphenyl)ethenesulfonamide,
respectively.

The amino-acid ester hydrochlorides used in this Example are either items of commerce, or they are prepared from the corresponding amino-acids (which are all items of commerce) by esterification. Procedures for the esterification of amino-acids are discussed by Greenstein and Winitz in the "Chemistry of the Amino-acids," John Wiley and Sons, Inc., New York-London, 1961, Volume 2, pp. 925–927.

EXAMPLE XVIII

When the procedure of Example XIV is repeated, and the DL-alanine methyl ester hydrochloride used therein is replaced by an equimolar amount of N-phenylglycine ethyl ester hydrochloride and N-p-chlorophenylglycine ethyl ester hydrochloride, respectively, this affords:
N-(N-phenyl-N-[ethoxycarbonylmethyl]carbamoyl)-2-phenylethenesulfonamide and
N-(N-[p-chlorophenyl]-N-[ethoxycarbonylmethyl]carbamoyl)-2-phenylethenesulfonamide, respectively.

EXAMPLE XIX

N-(Pyrrolidinocarbonyl)-2-phenylethenesulfonamide

A mixture of 3.4 g. of N-(N-[m-chlorophenyl]carbamoyl)-2-phenylethenesulfonamide and 2.15 g. of pyrrolidine in 100 ml. of ethanol is heated under reflux for 20 hours. The solution is cooled, and then it is concentrated in vacuo to ca. 25 ml. A small amount of starting material precipitates and it is filtered off. To the ethanol filtrate is then added 75 ml. of ether and 75 ml. of water. The layers are separated, and the aqueous layer is acidified using concentrated hydrochloric acid. This causes the crude product to precipitate. It is filtered off, and when dry it weighs 1.5 g. The ether layer is washed with 50 ml. of 1N hydrochloric acid, followed by 25 ml. of water. After being dried using anhydrous sodium sulfate, the ether is evaporated in vacuo to give a second crop of product (0.70 g.). The first crop of product is recrystallized from acetone to 0.60 g. of pure N-(pyrrolidinocarbonyl)-2-phenylethenesulfonamide, m.p. 201°–204° C.

Analysis — Calc'd for $C_{13}H_{16}N_2O_3S$ (percent): C, 55.71; H, 5.75; N, 10.00. Found (percent): C, 55.45; H, 5.68; N, 9.94.

EXAMPLE XX

Following the procedure of Example XIX and replacing the pyrrolidine by the appropriate amine, the following compounds are prepared:

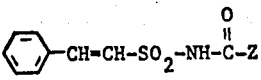

| Z | M.P. (°C.) | Calc'd (%) | | | Found (%) | | |
|---|---|---|---|---|---|---|---|
| | | C | H | N | C | H | N |
| N,N-dibutylamino | 104–105.5 | 60.34 | 7.74 | 8.28 | 60.60 | 7.50 | 8.32 |
| morpholino | 176–179 | 52.70 | 5.44 | 9.46 | 52.63 | 5.37 | 9.48 |
| 1,2,3,4-tetrahydro-isoquinolino | 165–167 | 63.15 | 5.30 | 8.18 | 63.00 | 5.35 | 8.26 |
| 3-azabicyclo[3.2.2]-nonan-3-yl | 181–184 | 61.06 | 6.63 | 8.38 | 61.08 | 6.66 | 8.32 |
| N,N-diethylamino | 110–113 | 55.31 | 6.43 | 9.92 | 55.28 | 6.29 | 9.80 |
| 4-hydroxypiperidino | 160–165 | 54.19 | 5.85 | 9.03 | 54.43 | 5.94 | 9.24 |
| N,N-diheptylamino | | 65.37 | 9.06 | 6.63 | 65.88 | 8.84 | 6.71 |

When N-(N,N-diphenylcarbamoyl)-2-phenylethenesulfonamide reacts with N,N-dipropylamine according to the procedure of Example XIX, the product is N-(N,N-dipropylcarbamoyl)-2-phenylethenesulfonamide, m.p. 128°–130° C.

Analysis — Calc'd for $C_{15}H_{22}N_2O_3S$ (percent): C, 58.05; H, 7.15; N, 9.03. Found (percent): C, 57.77; H, 7.09; N, 8.96.

Starting with N-(N-[m-tolyl]carbamoyl)-2-phenylethenesulfonamide and N,N-dibutylamine, and using the procedure of Example XIX, the product is N-(N,N-dibutylcarbamoyl)-2-phenylethenesulfonamide, m.p. 104°–105° C.

Analysis — Calc'd for $C_{17}H_{26}N_2O_3S$ (percent): C, 60.34; H, 7.74; N, 8.28. Found (percent): C, 60.23; H, 7.58; N, 8.50.

EXAMPLE XXI

N-(Piperidinocarbonyl)-2-phenylethenesulfonamide

A slurry of 6.5 g. of 2-phenylethenesulfonamide in 45 ml. of oxalyl chloride is stirred and refluxed for 16 hours. It is cooled to ambient temperature, and then the solid material is filtered off and washed with hexane. When dry, the solid weighs 2.2 g. and has a melting point of 170°–180° C.

The above solid is added in small portions with stirring at ambient temperature, to a solution of 5 ml. of piperidine in 15 ml. of methylene chloride. The mixture is stirred for an additional 1.5 hours after the end of the addition, and then it is evaporated to dryness, in vacuo. The residue is partitioned between 40 ml. of water and 25 ml. of ether, the layers are separated, and the other layer is discarded. The aqueous layer is acidified with acetic acid, and then it is extracted with ether. This latter ether extract is washed with water, dried using anhydrous sodium sulfate and then finally it is evaporated to dryness in vacuo. The residue is 0.60 g. of crude product, m.p. 138°–140° C. The crude product is recrystallized from a mixture of methylene chloride and ether, to give a pure sample of N-(N-piperidinocarbamoyl)-2-phenylethenesulfonamide, m.p. 175°–177° C.

Analysis — Calc'd for $C_{14}H_{18}N_2O_3S$ (percent): C, 57.13; H, 6.17; N, 9.52. Found (percent): C, 57.23; H, 6.11; N, 9.54.

EXAMPLE XXII

N-([4-Carboxypiperidino]carbonyl)-2-phenylethenesulfonamide

A mixture of 5 g. of N-(N,N-diphenylcarbamoyl)-2-phenylethenesulfonamide and 10.3 g. of ethyl isonipecotate in 20 ml. of N,N-dimethylformamide is maintained at ca. 90° C. for 40 minutes. The mixture is cooled to ambient temperature, diluted with ether, and then it is extracted with water. The water extract is acidified using concentrated hydrochloric acid, and then it is extracted with methylene chloride. The dried methylene chloride is evaporated to dryness in vacuo leaving a viscous oil. The oil is redissolved in a small volume of tetrahydrofuran, absorbed onto a column of silica gel, and then eluted from the column with an excess of the same solvent. The solvent is evaporated in vacuo, and the residue is dissolved in 50 ml. of 0.5N sodium hydroxide solution. After 1 hour it is reprecipitated by acidification, and recovered by vacuum filtration in the form of white crystals. It is then dissolved in a mixture of 100 ml. of acetone and 100 ml. of tetrahydrofuran, and the solution is concentrated slowly to effect precipitation of the product. The solid is filtered off, and then triturated with acetone to give pure N-([4-carboxypiperidino]carbonyl)-2-phenylethenesulfonamide, m.p. 179°–181° C.

Analysis — Calc'd for $C_{15}H_{18}N_2O_5S$ (percent): C, 53.25; H, 5.32 N, 8.28. Found (percent): C, 52.93; H, 5.58; N, 8.04.

EXAMPLE XXIII

N-(4-[3-Phenylpropyl]piperidinocarbonyl)-2-phenylethenesulfonamide

A solution of 12 g. of 4-(3-phenylpropyl)piperidine and 12.5 g. of the potassium salt of N-(N,N-diphenylcarbamoyl)-2-phenylethenesulfonamide (prepared as described in Example IV) in 30 ml. of N,N-dimethylformamide is heated to 75° C., and then 5.7 ml. of glacial acetic acid is added dropwise, with stirring. The temperature rises to 90° C. during the addition. The reaction mixture is maintained at 85°–87° C. for a further 45 minutes, and then it is allowed to cool to ambient temperature. It is poured onto a mixture of 200 ml. of 1N sodium hydroxide solution and 100 g. of crushed ice. A gummy precipitate forms. A 50-ml. portion of ether is added, and the mixture is stirred vigorously until a turbid solution is obtained. A 50-ml. portion of hexane is then added, which causes the sodium salt of the product to precipitate. It is filtered off and washed with water followed by ether. The crude sodium salt is redissolved in a mixture of 100 ml. of acetone and 50 ml. of water, and then 5 ml. of concentrated hydrochloric acid followed by 100 ml. of water is added. The precipitate which forms is filtered off, washed with aqueous acetone, and finally recrystallized from acetone-hexane to give 6.8 g. (55%) of pure N-(4-[3-phenylpropyl]piperidinocarbonyl)-2-phenylethenesulfonamide, m.p. 131°–133° C.

EXAMPLE XXIV

N-(N-[1-Carboxyprop-1-yl]carbamoyl)-2-phenylethenesulfonamide

To 30 ml. of 1N sodium hydroxide is added 1.0 g. of N-(N-[1-ethoxycarbonylprop-1-yl]carbamoyl)-2-phenylethenesulfonamide. The mixture is stirred at ambient temperature for 30 minutes, and then the small amount of insoluble material is filtered off and discarded. The filtrate is acidified using concentrated hydrochloric acid, which causes the product to precipitate. It is filtered off, washed with water, and then air dried to give 6.0 g. of N-(N-[1-carboxyprop-1-yl]carbamoyl)-2-phenylethenesulfonamide, m.p. 150°–152° C.

Analysis — Calc'd for $C_{13}H_{16}N_2O_5S$ (percent): C, 49.98; H, 5.16; N, 8.97. Found (percent): C, 49.72; H, 5.20; N, 8.85.

EXAMPLE XXV

Starting with the appropriate ester selected from those of Examples II, XII, XV and XVI, and using the hydrolysis procedure of Example, XXIV, the following compounds are prepared:

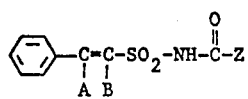

N-(N,N-di[carboxymethyl]carbamoyl)-2-phenylethenesulfonamide,
N-(N-[carboxymethyl]-N-methyl)carbamoyl)-2-phenylethenesulfonamide,
N-(N-[carboxymethyl]carbamoyl)-1-phenylpropene-2-sulfonamide,
N-(N-[carboxymethyl]carbamoyl)-2-phenylpropene-1-sulfonamide,
N-(N-[carboxymethyl]carbamoyl)-2-(p-chlorophenyl)-ethenesulfonamide,
N-(N-[carboxymethyl]carbamoyl)-1,1-diphenylethenesulfonamide,
N-(N-[carboxymethyl]carbamoyl)-2-(p-tolyl)ethenesulfonamide,
N-(N-[carboxymethyl]carbamoyl)-2-(m-chlorophenyl)ethenesulfonamide,
N-(N-[carboxymethyl]carbamoyl)-2-(p-bromophenyl)ethenesulfonamide,
N-(N-[carboxymethyl]carbamoyl)-1-(m-methoxyphenyl)propene-2-sulfonamide,
N-(N-[1-carboxyethyl]carbamoyl)-2-(p-fluorophenyl)-ethenesulfonamide,
N-(N-[1-carboxyethyl]carbamoyl)-3-phenylbut-2-ene-2-sulfonamide,
N-(N-[1-carboxyethyl]carbamoyl)-2-phenylbut-1-ene-1-sulfonamide,
N-(N-[1-carboxyethyl]carbamoyl)-2-(p-chlorophenyl)propene-1-sulfonamide,
N-(N-[1-carboxyethyl]carbamoyl)-2-(p-isopropylphenyl)propene-1-sulfonamide,

| A | B | Z | M.P. (°C.) | Calc'd (%) C | H | N | Found (%) C | H | N |
|---|---|---|---|---|---|---|---|---|---|
| H | H | N-(1-carboxy-2-phenylethyl)amino | 167.5–169 | 57.75 | 4.85 | 7.48 | 57.64 | 4.84 | 7.22 |
| H | H | N-(carboxymethyl)amino | 182–183 | 46.48 | 4.26 | 9.86 | 46.69 | 4.33 | 9.86 |
| H | CH₃ | N-(carboxymethyl)amino | 183–185 | 48.32 | 4.73 | 9.39 | 47.99 | 4.79 | 9.29 |
| H | H | N-(1-carboxyethyl)amino | 155–156 | 48.32 | 4.73 | 9.39 | 48.31 | 4.71 | 9.14 |
| H | H | N-(1-carboxy-3-methylbut-1-yl)amino | 162–164 | 52.92 | 5.87 | 8.23 | 52.56 | 5.75 | 8.02 |
| H | H | N-(1,3-dicarboxyprop-1-yl)amino | 170–171 | 47.19 | 4.53 | 7.86 | 46.98 | 4.51 | 7.79 |
| H | H | N-(1-carboxy-2-methylprop-1-yl)amino | 155–157 | 51.52 | 5.56 | 8.58 | 51.33 | 5.74 | 8.47 |
| H | H | N-(3-carboxyprop-1-yl)amino | 133–135 | 49.98 | 5.16 | 8.97 | 49.82 | 5.22 | 8.82 |
| H | H | N-(1-carboxypent-1-yl)amino | 140–142 | 52.92 | 5.92 | 8.23 | 58.85 | 6.00 | 8.22 |
| H | H | N-(5-carboxypent-1-yl)amino | 154–155.5 | 52.92 | 5.92 | 8.23 | 53.07 | 5.98 | 8.17 |
| H | H | N-(1-carboxy-2-methylbut-1-yl)amino* | 130–133 | 50.40 | 5.92 | 7.83 | 50.69 | 5.71 | 7.87 |
| H | H | N-(1-carboxyhept-1-yl)amino | 142–144 | 55.41 | 6.57 | 7.60 | 55.86 | 6.70 | 7.37 |
| H | H | N-(carboxymethyl)-N-benzylamino | 127–128 | 57.75 | 4.85 | 7.48 | 57.40 | 4.82 | 7.20 |

*This material is isolated, and analyzed as a monohydrate.

EXAMPLE XXVI

Starting with the appropriate ester, selected from those of Examples III, XII, XVII and XVIII, and using the hydrolysis procedure of Example XXIV, the following compounds are prepared:

N-(N-[carboxymethyl]carbamoyl)-2-(m-methoxyphenyl)propene-1-sulfonamide,
N-(N-[carboxymethyl]carbamoyl)-2-(p-biphenylyl)-propene-1-sulfonamide,
N-(N-[1-carboxy-2-methylbut-1-yl]carbamoyl)-2-phenylpropene-1-sulfonamide,
N-(N-[1-carboxy-2-methylbut-1-yl]carbamoyl)-2-(o-chlorophenyl) ethenesulfonamide,
N-(N-[1-carboxy-2-methylbut-1-yl]carbamoyl)-1-phenylbut-1-ene-2-sulfonamide,
N-(N-[1-carboxy-2-methylbut-1-yl]carbamoyl)-1,2-diphenylethenesulfonamide,
N-(N-[7-carboxyhept-1-yl]carbamoyl)-2-phenylethenesulfonamide, N-(N-[7-carboxyhept-1-yl]carbamoyl)-1-(m-chlorophenyl)propene-2-sulfonamide, N-(N-[7-carboxyhept-1-yl]carbamoyl-2-(m-tolyl)ethenesulfonamide, N-(N-[7-carboxyhept-1-yl]carbamoyl)-2-(p-isopropoxyphenyl)ethenesulfonamide, N-(N-phenyl-N-[carboxymethyl]carbamoyl)-2-phenylethenesulfonamide and N-(N-[p-chlorophenyl]-N-[carboxymethyl]carbamoyl)-2-phenylethenesulfonamide, respectively.

EXAMPLE XXVII

N-(N-[1-carboxyhetp-1-yl]carbamoyl)-2-phenylethenesulfonamide

To 40 ml. of N,N-dimethylformamide is added 10.05 g. of ethyl 2-aminooctanoate hydrochloride followed by 2.1 g. of a 56.6% dispersion of sodium hydride in mineral oil. The mixture is stirred at ambient temperature for 15 minutes, and then 7.6 g. of N-(N,N-diphenylcarbamoyl)-2-phenylethenesulfonamide is added. The reaction mixture is then heated at ca. 100°C. for 1 hr. After being allowed to cool back to ambient temperature, the mixture is diluted with an excess of ether and then it is extracted with water. When the water extract is acidified using concentrated hydrochloric acid, an oil separates. The supernatant aqueous layer is decanted off, and replaced by 50 ml. of ether and 50 ml. of fresh water. The ether layer is removed, dried using anhydrous sodium sulfate, and then evaporated in vacuo. The residue is an oil, which resists attempts to induce it to solidify. The oil is dissolved in acetone, and 50 ml. of 1N sodium hydroxide is added. A heterogeneous mixture is formed, which is stirred at ambient temperature overnight. The mixture is then extracted with ether, and the extract is discarded. The residual aqueous phase is acidified using concentrated hydrochloric acid, and the oil which precipitates is extracted into ether. The etheral solution is dried (Na$_2$SO$_4$), treated with decolorizing charcoal, and then evaporated in vacuo. An oil is obtained, which slowly crystallizes on standing. The solid produced is triturated under benzene, filtered off, and dried, giving 3.0 g. of N-(N-[1-carboxyhept-1-yl]-carbamoyl)-2-phenylethenesulfonamide, m.p. 142°–144°C.

Analysis — Calc'd for C$_{17}$H$_{24}$N$_2$O$_5$S (percent): C, 55,41; H, 6.57; N, 7.60. Found (percent): C, 55.86; H, 6.70; N, 7.37.

EXAMPLE XXVIII

N-(4-[3-(p-hydroxyphenyl)propyl]piperidinocarbonyl)-2-phenylethenesulfonamide

To a solution of 1.37 g. of N-(4-[3-(p-methoxyphenyl)propyl]piperidinocarbonyl)-2-phenylethenesulfonamide in 30 ml. of methylene chloride is added 175 μl. of glacial acetic acid. The mixture is cooled to −60° C., and then 850 μl. of boron tribromide is added slowly. The reaction mixture is then allowed to warm to ambient temperature. After a further 3 hours, it is washed with ice-cold water, and then it is extracted with 1N sodium hydroxide. The sodium hydroxide extract is washed with ether and then it is acidified using concentrated hydrochloric acid. This causes a gum to precipitate. The supernatant aqueous layer is poured off, and the gum is dissolved in methylene chloride. The solvent is dried using anhydrous sodium sulfate, and then evaporated in vacuo to give 0.50 g. of crude product. The product is purified by dissolving it in a small volume of acetone and reprecipitating it by adding hexane. Finally there is obtained 0.142 g. of pure N-(4-[3-(p-hydroxyphenyl)propyl]piperidinocarbonyl)-2-phenylethenesulfonamide, m.p. 132–5° C.

Analysis — Calc'd for C$_{23}$H$_{28}$N$_2$O$_4$S (percent): C, 64.47; H, 6.59; N, 6.54. Found (percent): C, 64.08; H, 6.97; N, 6.40.

EXAMPLE XXIX

Reaction of the appropriate N-([(methoxyphenyl)alkyl]piperidinocarbonyl)alkenesulfonamide with boron tribromide, according to the procedure of Example XXVIII, produces the following compounds:

N-(4-[3-(m-hydroxyphenyl)propyl]piperidinocarbonyl)-2-phenylethenesulfonamide,

N-(4-[3-(o-hydroxyphenyl)propyl]piperidinocarbonyl)-2-phenylethenesulfonamide,

N-(4-[2-(p-hydroxyphenyl)ethyl]piperidinocarbonyl-2-(p-chlorophenyl)ethenesulfonamide, N-(4-[4-(m-hydroxyphenyl)butyl]piperidinocarbonyl)-1-(p-tolyl)propene-2-sulfonamide and N-(4-[5-(m-hydroxyphenyl)pentyl]piperidinocarbonyl)-2-(p-bromophenyl)ethenesulfonamide, respectively.

EXAMPLE XXX

N-(4-[3-Phenylpropyl]piperidinocarbonyl)-2-phenylethenesulfonamide

A stirred mixture of 1.83 g. of 2-phenylethenesulfonamide, 1.3 ml. of oxalyl chloride and 15 ml. of tetrahydrofuran is heated in an oil bath at 75°–80°C. for 1.5 hours, under an atmosphere of nitrogen. To the solution obtained, is added 30 ml. of xylene, and the internal temperature is raised to 138°C. over a 20 minute period, while allowing the tetrahydorfuran and excess oxalyl chloride to distil out of the solution. During this period, two further 5-ml. portions of xylene are added. The resulting solution is maintained at ca. 138°C. for a further 15 minutes, and then it is cooled to 85°C. To this xylene solution of 2-phenylethenesulfonyl isocyanate is added 4.06 g. of 4-(3-phenylpropyl)piperidine in small portions during 1 minute. The reaction mixture is stirred at ambient temperature for 1.5 hours, and then it is washed successively with 75 ml. of 1N hydrochloric acid and two 25-ml. portions of water. To the dried and filtered xylene solution, is then added 20 ml. of acetone followed by the dropwise addition of 120 ml. of hexane. The precipitate which forms is removed by filtration, affording 2.89 g. (70% yield) of crude product. After recrystallization from acetone/hexane, there is obtained 1.07 g. of the title compound showing a melting point of 125°–127°C.

EXAMPLE XXXI

Reaction of the appropriate alkenesulfonamide with oxalyl chloride, according to the procedure of Example XXX affords the following isocyanates:

2-(o-fluorophenyl)ethenesulfonyl isocyanate,
2-(p-chlorophenyl)ethenesulfonyl isocyanate,
2-(p-bromophenyl)ethenesulfonyl isocyanate,
2-(m-tolyl)propene-1-sulfonyl isocyanate,
1-(p-methoxyphenyl)butene-2-sulfonyl isocyanate and
2-(p-trifluoromethylphenyl)ethenesulfonyl isocyanate, respectively.

Reaction of one of the above isocyanates with the requisite amine, also according to the procedure of Example XXX, produces the following compounds.

N-(4-[3-phenylpropyl]piperidinocarbonyl)-2-(2-fluorophenyl)ethenesulfonamide,

N-(4-[3-(p-tolyl)propyl]piperidinocarbonyl)-2-(p-chlorophenyl)ethenesulfonamide, N-(4-[5-(m-methoxyphenyl)pentyl]piperidinocarbonyl)-2-(p-bromophenyl)ethenesulfonamide, N-(2-methylpiperidinocarbonyl)-2-(m-tolyl)propene-1-sulfonamide, N-(1,2,3,4-tetrahydroisoquinolinocarbonyl)-1-(p-methoxyphenyl)butene-2-sulfonamide and N-(N,N-dibutylcarbamoyl)-2-(p-trifluoromethylphenyl)ethenesulfonamide, respectively.

EXAMPLE XXXII

N-(4-[3-Phenylpropyl]piperidinocarbonyl)-2-phenylethenesulfonamide

A stirred mixture of 1.83 g. (0.01 mole) of 2-phenylethenesulfonamide, 3.45 g. (0.025 mole) of potassium carbonate and 4.0 g. (0.015 mole) of 4-(3-phenylpropyl)piperidinocarbonyl chloride, in 75 ml. of chloroform is heated under reflux for 22 hours. The solvent is then removed by evaporation in vacuo, and to the residue is added 75 ml of 0.5N sodium hydroxide and 35 ml. of ether. The mixture is stirred for 1 hour, and then the solid which remains undissolved is removed by filtration. This affords 1.84 g. (ca. 41% yield) of the title compound as a mixture of its sodium and potassium salts.

A 0.5-g. portion of the above crude product is dissolved in 6 ml. of acetone and 3 ml. of water. The pH of the mixture is lowered to 2.0, and the undissolved solid is removed by filtration. It is then recrystallized from acetone-hexane, giving 0.28 g. of the title compound, having melting point 127.5°–129°C.

EXAMPLE XXXIII

N-(4-[3-Phenylpropyl]piperidinocarbonyl)-2-phenylethenesulfonamide

A solution of 1.77 g. (7.5 mmole) of N-(N-propylcarbamoyl)-2-phenyl ethenesulfonamide, 3.0 g. (15 mmole) of 4-(3-phenylpropyl)piperidine and 0.86 ml. (15 mmole) of acetic acid, in 10 ml. of N,N-dimethylformamide is heated at 100°–105°C. for 4 hours. The reaction solution is then cooled to 25°C., and 50 ml. of 1N hydrochloric acid, followed by 50 ml. of ether is added. The layers are separated, and to the ether phase is added 50 ml. of 1N sodium hydroxide. This causes an oil to appear as an intermediate phase. The three layers are separated, and the aqueous phase is discarded. The ether phase is washed with water and then evaporated in vacuo to give 2.3 g. of a viscous liquid. The intermediate oil phase is dissolved in 25 ml. of water, which is then acidified with concentrated hydrochloric acid. The acidified aqueous phase is extracted with ethyl acetate, and the extracts are washed with water and then evaporated in vacuo. This affords 0.5 g. of a gummy residue.

The 2.3 g. of oil and the 0.5 g. of gummy residue are combined and chromatographed on a column of silica gel. The first few fractions are combined and evaporated in vacuo, to give 0.3 g. of an oil. This latter oil is dissolved in 5 ml. of acetone, and 5 ml. of 1N sodium hydroxide, followed by 10 ml. of water, is added. This causes the crude product to precipitate as its sodium salt. The sodium salt is dissolved in 3 ml. of acetone, and 5 drops of concentrated hydrochloric acid, followed by 10 ml. of water, are added. This solution is extracted with ethyl acetate. The dried extract is evaporated in vacuo, and the residue is recrystallized from acetone-hexane, giving 12 mg. of the title compound, m.p. 119°–122°C. After two further recrystallizations from acetone-hexane, the product has a melting point of 127.5°–129.5°C.

EXAMPLE XXXIV

A dry solid pharmaceutical composition is prepared by blending the following materials together in the specified proportions by weight:

| | |
|---|---|
| N-(1,2,3,4-tetrahydroisoquinolinocarbonyl)-2-phenylethenesulfonamide | 50 |
| sodium citrate | 25 |
| alginic acid | 10 |
| polyvinylpyrrolidone | 10 |
| magnesium stearate | 5 |

After the dried composition is thoroughly blended, tablets are punched from the mixture, each tablet being of such size as to contain 100 mg. of the active ingredient.

Tablets are also prepared containing respectively 10, 25, 50 and 200 mg. of active ingredient, by chosing the appropriate proportions of N-(1,2,3,4-tetrahydroisoquinolinocarbonyl)-2-phenylethenesulfonamide and the excipient blend in each case.

EXAMPLE XXXV

A dry solid pharmaceutical composition is prepared by combining the following materials in the indicated proportions by weight:

| | |
|---|---|
| N-(4-[3-phenylpropyl]piperidinocarbonyl)-2-phenylethenesulfonamide | 250.0 |
| lactose | 190.2 |
| dried corn starch | 50.0 |
| Sterotex K (a hydrogenated vegetable oil) | 9.8 |

The dry mixture is thoroughly agitated to obtain a completely uniform blend. Soft elastic and hard gelatin capsules containing this composition are then prepared, employing sufficient material to provide each capsule with 250 mg. of active ingredient.

Capsules are also prepared containing respectively 50, 100 and 500 mg. of active ingredient, by varying the proportions of sulfonamide and excipient blend.

EXAMPLE XXXVI

To a stirred solution of 4.12 g. of N-(4-[3-phenylpropyl]piperidinocarbonyl)-2-phenylethenesulfonamide in 100 ml. of n-butanol, is added a solution prepared by dissolving 390 mg. of potassium in 10 ml. of n-butanol. The mixture is stirred for an additional 15 minutes, and then the solvent is removed by evaporation in vacuo. To the residue is added 250 ml. of diethyl ether, and the mixture is stirred for 15 minutes. The solid is then filtered off, and dried under vacuum, giving the potassium salt of N-(4-[3-phenylpropyl]piperidinocarbonyl)-2-phenylethenesulfonamide.

EXAMPLE XXXVII

Normal, Sprague-Dawley (Charles River), male rats are fasted for 9 hours. Test groups, each consisting of 5 animals, are then fed overnight (15–16 hours) with ground Purina rat chow, containing 0.2% of the test compound. The following morning, the medicated food is withdrawn, and then, after 1 hour, each rat is dosed with an oral gavage containing 50 mg./kg. of the test compound. After a further 2 hours, a 300-mg./kg. dose of Triton WR-1339 (oxyethylated tertiaryoctylphenol-formaldehyde polymer, Ruger Chemical Co., Philadelphia, Pa.) in saline is administered to each rat, by injection into the tail vein. After a further 2 hours, a second oral gavage containing 50 mg./kg. of the test compound is given to each rat. After a further 4 hours, each rate is exxanguinated via the abdominal aorta under pentobarbital anesthesia. Control rats are treated in the same manner, except that they receive rat chow alone, and the two oral gavages contain no test compound. Control rats receive the same dose of Triton as the test animals.

Plasma is obtained fom the heparinized blood samples, and the plasma cholesterol concentrations are measured using the Auto-Analyser (Technicon method N-24a). The activity of a test compound is assessed by comparing plasma cholesterol levels from rats treated with the test compound and control rats. Results are shown below in Tabular form. The reported results are calculated by subtracting the plasma cholesterol concentration in treated rats from the control plasma cholesterol level, and expressing the difference as a percentage of the control value.

| Test Compound | Percentage Cholesterol Fall |
|---|---|
| N-(N-n-butylcarbamoyl)-2-(p-chlorophenyl)ethenesulfonamide | 8 |
| N-(piperidinocarbonyl)-2-phenylethenesulfonamide | 5 |
| N-(N-[carboxymethyl]carbamoyl)-2-phenylethenesulfonamide | 8 |
| N-(N-cyclohexylcarbamoyl)-2-phenylethenesulfonamide | 14 |
| N-(N-[ethoxycarbonylmethyl]carbamoyl)-2-phenylethenesulfonamide | 9 |
| N-(N,N-di[n-butyl]carbamoyl)-2-phenylethenesulfonamide | 5 |
| N-(4-benzylpiperidinocarbonyl)-2-phenylethenesulfonamide | 5 |
| N-(N-n-propylcarbamoyl)-1,1-diphenylethenesulfonamide | 12 |
| N-(N-allylcarbamoyl)-2-phenylethenesulfonamide | 21 |
| N-(N-methyl-N-[2-phenylethyl]carbamoyl)-2-phenylethenesulfonamide | 13 |
| N-(1-azacycloheptylcarbonyl)-2-phenylethenesulfonamide | 16 |
| N-(N,N-di[2-methylprop-1-yl]carbamoyl)-2-phenylethenesulfonamide | 15 |
| N-(morpholinocarbonyl)-1-phenylpropene-2-sulfonamide | 8 |
| N-(N-[1-ethoxycarbonyl-2-methylprop-1-yl[-carbamoyl)-2-phenylethenesulfonamide | 15 |
| N-(4-[3-phenylpropyl]piperidinocarbonyl)-2-phenylethenesulfonamide | 30 |
| '' | 17 |
| '' | 20 |
| '' | 31 |

EXAMPLE XXXVIII

A normal, adult, beagle dog, weighing approximately 10 kg., is fed Purina dog chow once daily, at 12:00 noon, for several days. Then on the mornings of two consecutive days, the dog is bled from the jugular vein, and the plasma cholesterol concentrations are measured by the method adapted for use in the Technicon Auto-Analyser. The mean of these values constitutes the baseline plasma cholesterol level of that dog. The dog is then dosed orally, twice daily, with the test compound, while continuing to feed the dog Purina dog chow once daily at 12:00 noon. On the morning of the sixth day after the start of administration of the test compound, the dog is again bled from the jugular vein, and again the plasma cholesterol level is measured using the Technicon Auto-Analyser. The level thus obtained is compared with the baseline value, in determining the hypolipidemic properties of the test compound. Results are shown below.

| Compound | Dosage of Test Compound (mg./kg.) | Sex of Dog | Plasma Cholesterol Level (mg./100 ml.) | |
|---|---|---|---|---|
| | | | Baseline | After administration of test compound for 6 days |
| N-(N-[n-butyl]carbamoyl)-2-phenylethenesulfonamide | 25 | F | 296 | 202 |
| '' | 25 | M | 143 | 132 |
| N-(N-[m-tolyl]carbamoyl)-2-phenylethenesulfonamide | 25 | F | 149 | 129 |
| '' | 25 | M | 135 | 94 |
| N-(N-[n-butyl]carbamoyl)-1-phenylpropene-2-sulfonamide | 25 | F | 157 | 136 |
| '' | 25 | M | 130 | 128 |
| N-(1,2,3,4-tetrahydroisoquinolinocarbonyl)-2-phenylethenesulfonamide | 25 | F | 176 | 138 |
| '' | 25 | M | 155 | 84 |
| '' | 2.5 | M | 137 | 128 |
| '' | 2.5 | M | 159 | 146 |
| '' | 1 | F | 160 | 157 |
| '' | 1 | M | 190 | 143 |
| N-(4-[3-phenylpropyl]piperidinocarbonyl)-2-phenylethenesulfonamide | 5 | F | 120 | 114 |
| '' | 5 | F | 150 | 125 |
| '' | 5 | M | 152 | 127 |
| '' | 5 | M | 123 | 106 |
| '' | 1 | F | 170 | 156 |
| '' | 1 | F | 180 | 157 |
| '' | 1 | M | 170 | 141 |
| '' | 1 | M | 150 | 118 |
| N-(N-[carboxymethyl]carbamoyl)-2-phenylethenesulfonamide | 5 | F | 140 | 118 |
| '' | 5 | F | 150 | 210 |

| Compound | Dosage of Test Compound (mg./kg.) | Sex of Dog | Plasma Cholesterol Level (mg./100 ml.) | |
|---|---|---|---|---|
| | | | Baseline | After administration of test compound for 6 days |
| " | 5 | M | 140 | 140 |
| " | 5 | M | 170 | 167 |

The following Preparations are provided, for the purpose of illustrating the source of certain starting materials used in the foregoing Examples.

PREPARATION A

1-Phenylpropene-2-sulfonamide

To 17.5 ml. of N,N-dimethylformamide, cooled to 15°C., is added dropwise, with stirring, during 30 minutes, 15.5 ml. of sulfuryl chloride. The temperature is maintained below 25°C during the addition. The mixture is stirred for an additional 30 minutes at 25°C., and then 11.3g. of 1-phenylpropene is added. The reaction mixture is heated at 90°–93°C. for 75 minutes. It is then poured onto 400g. of crushed ice, and the product is extracted into methylene chloride. The solvent is dried using anhydrous sodium sulfate, and then it is evaporated in vacuo to give 18.7g. of 1-phenylpropene-2-sulfonyl chloride as a liquid.

The 1-phenylpropene-2-sulfonyl chloride is added to 200 ml. of concentrated ammonium hydroxide. After 1 hour the crystalline precipitate which has formed is filtered off, and washed sequentially with water and hexane. The crude product so obtained is partitioned between 150 ml. of 1N sodium hydroxide and 50 ml. of ether, giving two clear phases. The ether phase is removed and washed with 50 ml. of water, and then the water wash is added to the original aqueous phase. This combined solution is acidified using concentrated hydrochloric acid, which causes the product to precipitate. It is filtered off, and after drying this affords 10.9g. of 1-phenylpropene-2-sulfonamide, m.p. 138°–139.5°C.

PREPARATION B

Following the procedure of Preparation A, 2-phenylpropene is reacted with sulfuryl chloride in N,N-dimethylformamide to give 2-phenylpropene-1-sulfonyl chloride, which is then treated with ammonia to give 2-phenylpropene-1-sulfonamide, m.p. 101°–102.5°C.

When 1,1-diphenylethene reacts with sulfuryl chloride in N,N-dimethylformaide, followed by treatment with ammonia, according to the procedure of Preparation A, there is obtained 2,2-diphenylethenesulfonamide, m.p. 134°–135°C.

Analysis— Calcd. for $C_{14}H_{13}NO_2S$ (percent): C, 64.86; H, 5.05; N, 5.40. Found (percent): C, 64.73; H, 5.02; N, 5.26.

PREPARATION C

The procedure of Preparation A is repeated, except that the 1-phenylpropene used therein is replaced by an equimolar amount of the appropriate phenylethene, phenylpropene, phenylbutene or diphenylethene derivative to produce the following sulfonamides:

2-phenylbut-1-ene-1-sulfonamide,
2-(p-chlorophenyl)propene-1-sulfonamide,
2-(p-methoxyphenyl)propene-1-sulfonamide,
1-(m-chlorophenyl)propene-2-sulfonamide,
2-(p-chlorophenyl)but-1-ene-1-sulfonamide,
1,2-diphenylethenesulfonamide,
3-phenylbut-2-ene-2-sulfonamide,
1-(p-chlorophenyl)propene-2-sulfonamide,
1,2-diphenylpropene-1-sulfonamide,
2-(p-tolyl)propene-1-sulfonamide,
2-(p-isopropylphenyl)propene-1-sulfonamide,
1-(p-ethoxyphenyl)propene-2-sulfonamide,
2-(p-fluorophenyl)propene-1-sulfonamide,
2-(p-butoxyphenyl)propene-1-sulfonamide,
1-phenylbut-1-ene-2-sulfonamide,
3-(m-chlorophenyl)but-2-ene-2-sulfonamide,
2-(p-chlorophenyl)-2-phenylethenesulfonamide,
2-(p-n-butylphenyl)propene-1-sulfonamide,
2-(m-methoxyphenyl)propene-1-sulfonamide,
2-(p-biphenylyl)propene-1-sulfonamide,
2,2-diphenylethenesulfonamide,
2-(m-chlorophenyl)propene-1-sulfonamide,
2-(m-bromophenyl)propene-1-sulfonamide,
2-(m-tolyl)propene-1-sulfonamide,
1-(o-chlorophenyl)propene-2-sulfonamide,
1-(p-fluorophenyl)propene-2-sulfonamide,
1-(p-tolyl)propene-2-sulfonamide,
1-(m-methoxyphenyl)propene-2-sulfonamide,
2-(p-tolyl)but-1-ene-1-sulfonamide,
2-(m-methoxyphenyl)but-1-ene-1-sulfonamide,
1-(p-chlorophenyl)but-1-ene-2-sulfonamide,
1-(m-methoxyphenyl)but-1-ene-2-sulfonamide and
3-(p-chlorophenyl)but-2-ene-2-sulfonamide, respectively.

PREPARATION D

N,N-Diphenylcarbamoyl chloride is reacted with N-(endo-7-oxabicyclo[2.2.1]heptan-2-ylmethyl)amine, essentially according to the procedure given McManus et al., J. Med. Chem., 8, 766 (1965), for the preparation of 1,1-diphenyl-3-cycloheptylurea. The product is 1,1-diphenyl-3-(endo-7-oxabicyclo[2.2.1-]heptan-2-ylmethyl)urea, m.p. 109°–111°C.

Analysis— Calcd. for $C_{20}H_{22}N_2O_2$ (percent): C, 74.49; H, 6.89; N, 8.68. Found (percent): C, 74.28; H, 6.93; N, 8.61.

In a similar manner, N,N-diphenylcarbamoyl chloride and N-(exo-7-oxabicyclo[2.2.1]heptan-2-ylmethyl)amine react to produce 1,1-diphenyl-3-(exo-7-oxabicyclo[2.2.1]heptan-2-ylmethyl)urea, m.p. 128°–130°C.

Analysis— Calcd. for $C_{20}H_{22}N_2O_2$ (percent): C, 74.49; H, 6.89; N, 8.68. Found (percent): C, 74.70; H, 6.75; N, 8.87.

PREPARATION E

Endo. and exo-isomers of N-(7-oxabicyclo[2.2.1]heptan-2-ylmethyl)amine

To a stirred solution of 212g. of acrylonitrile, 272g. of furan and 50 mg. of hydroquinone, in 1 liter of benzene, is added a solution of 55 ml. of titanium tetrachloride in 500 ml. of benzene. The addition is carried out at such a rate that the internal reaction temperature does not exceed 35°C. The reaction mixture is then stirred at ambient temperature for 5 days. It is then treated with 500 ml. of 0.5N hydrochloric acid. After filtration, the aqueous phase is removed and extracted with benzene. The two benzene solutions are then combined, washed with water, dried using anhydrous sodium sulfate, and then evaporated in vacuo. This affords 156.3g. of a mixture of endo- and exo-7-oxabicyclo[2.2.1]hept-2-en-5ylcyanide.

A 130-g. sample of the above mixture of isomers is dissolved in 1 liter of acetone, and hydrogenated at 50 p.s.i. in the presence of 2g. of palladium-on-barium sulfate. The catalyst is removed by filtration, and the solvent by evaporation under reduced pressure. The residual oil is fractionally distilled to give 55.5g. of pure endo-7-oxabicyclo[2.2.1]heptan-2-ylcyanide, b.p. 45°C. (0.1 mm. Hg), and 37.9g. of pure exo-7-oxabicyclo[2.2.1]heptan-2-ylcyanide, b.p. 48°C. (0.02 mm. Hg). A small fraction weighing 14.7g., and consisting of an endo-exo mixture, is also obtained.

Analysis.— Calcd. for $C_7H_9NO$ (percent): C, 68.27; H, 7.37; N, 11.37. Found for endo-isomer (percent): C, 67.96; H, 7.21; N, 11.37. Found for exo-isomer (percent): C, 68.32; H, 7.42; N, 11.64.

To a stirred solution of 54.3g. of endo-7-oxabicyclo[2.2.1]heptan-2-ylcyanide in 500 ml. of methanol, is added 24 ml. of a slurry of Raney nickel in methanol, followed by the dropwise addition of a solution of 33.2g. of sodium borohydride in 11- ml. of 4N sodium hydroxide. During the latter addition step, external cooling is applied to maintain an internal temperature of 40°–50°C. At the end of the addition the mixture is stirred for a further 20 minutes, and then the solids are filtered off. The filtrate is evaporated in vacuo, and the residue obtained is suspended in 500 ml. of 1N sodium hydroxide. The mixture is extracted several times with chloroform, and then the combined extracts are dried and evaporated giving 55.5g. of N-(endo-7-oxabicyclo[2.2.1]heptan-2-ylmethyl)amine, b.p. 90°C. (10mm. Hg).

A sample of exo-7-oxabicyclo[2.2.1]heptan-2-ylmethylcyanide is reduced by treatment with Raney nickel and sodium borohydride in methanol as described for the endo-isomer. There is obtained a high yield of N-(exo-7-oxabicyclo[2.2.1]heptan-2-ylmethyl)amine, b.p. 92°–96°C. (14-16mm. Hg).

PREPARATION F

4-(3-[p-Methoxyphenyl]propyl)pyridine

To a stirred solution of 3.04 g. of 2-(p-methoxyphenyl)ethanol in 10 ml. of benzene, is added dropwise, a solution of 0.72 ml. of phosphorus tribromide in 10 ml. of benzene, at ambient temperature. The mixture is then heated at 60°C. for 1 hour. After being cooled to ambient temperature again, the reaction mixture is poured onto 50 g. of crushed ice. A small amount of ether is added, and then the organic phase is separated off, washed sequentially with 0.5N sodium hydroxide and water, and evaporated to dryness. This affords 2.8 g. of 2-(p-methoxyphenyl)ethyl bromide as an oil.

The above oil is dissolved in 15 ml. of ether, which is then added dropwise to 243 mg. of magnesium turnings covered with 10 ml. of ether. A few crystals of iodine are added, and then the solvent is refluxed until almost all the magnesium has reacted. This gives an ethereal solution of 2-(p-methoxyphenyl)ethylmagnesium bromide.

The above-described Grignard solution is added dropwise, at 0°C., to a stirred solution of 1.04 g. of 4-cyanopyridine in 15 ml. of ether. At the end of the addition, the reaction mixture is refluxed for 4 hours and then it is stirred at ambient temperature overnight. The reaction is quenched with ice water, and the aqueous phase is acidified using concentrated hydrochloric acid. The aqueous phase is then separated off, and heated at 85°–90°C. for 1 hour. It is cooled back to ambient temperature, and extracted with chloroform, followed by ether. The combined organic extracts are dried using anhydrous magnesium sulfate, and then evaporated in vacuo, giving the product as an orange-colored oil. The product is 2-(p-methoxyphenyl)ethyl 4-pyridyl ketone.

The above-described ketone (800 mg.) is heated under reflux for 2 hours with 850 mg. of hydrazine hydrate. At this point 1.6 g. of powdered potassium hydroxide is added and the reflux is continued for a further 2 hours. The reaction mixture is then cooled to ambient temperature, diluted with 20 ml. of water, and extracted with ether. The dried ether extract is evaporated to dryness, leaving 260 mg. of 4-(3-[p-methoxyphenyl]propyl)pyridine.

PREPARATION G

Starting with the appropriate cyanopyridine and (hydroxyalkyl)benzene compound, and following the procedure of Preparation F, the following compounds are produced:

3-(3-phenylpropyl)pyridine,
2-(3-phenylpropyl)pyridine,
4-(2-[p-isopropoxyphenyl]ethyl)pyridine,
3-(3-[p-butoxyphenyl]propyl)pyridine,
4-(3-[p-isopropylphenyl]propyl)pyridine,
4-(3-[p-tert-butylphenyl]propyl)pyridine,
4-(m-methylbenzyl)pyridine,
4-(3-[m-methoxyphenyl]propyl)pyridine,
4-(3-[o-methoxyphenyl]porpyl)pyridine,
4-(2-[p-methoxyphenyl]ethyl)pyridine,
4-(4-[m-methoxyphenyl]butyl)pyridine,
4-(3-[p-tolyl]propyl)pyridine,
4-(5-[m-methoxyphenyl]pentyl)pyridine,
4-(4-phenylbutyl)pyridine,
4-(5-phenylpentyl)pyridine,
4-(2-phenylprop-1-yl)pyridine and
4-(2-phenylbut-1-yl)pyridine,
respectively

PREPARATION H

4-(3-[p-Methoxyphenyl]propyl)piperidine

A solution of 2.27 g. of 4-(3-[p-methoxyphenyl]propyl)piperidine in 50 ml. of 1.0N hydrochloric acid is hydrogenated at 45 psi, at ambient temperature, in the presence of 150 mg. of platinum oxide. After 20 hours the theoretical amount of hydrogen has been absorbed, and the catalyst is filtered off. The aqueous filtrate is basified with 5N sodium hydroxide, and then it is extracted with ether. The extract is dried and evaporated in vacuo, leaving 2.2 g. of an oil. The oil slowly solidifies, giving 4-(3-[p-methoxyphenyl]propyl)piperidine, mp 65°–70°C.

PREPARATION I

Hydrogenation of the pyridine derivatives listed in Preparation G, according to the procedure of Preparation H, produces the following piperidine compounds:

3-(3-phenylpropyl)piperidine,
2-(3-phenylpropyl)piperidine,
4-(2-[p-isopropoxyphenyl]ethyl)piperidine
3-(3-[p-butoxyphenyl]propyl)piperidine,
4-(3-[p-isopropylphenyl]propyl)piperidine,
4-(3-[p-tert-butylphenyl]propyl)piperidine,
4-(m-methylbenzyl)piperidine
4-(3-[m-methoxyphenyl]propyl)piperidine,
4-(3-[o-methoxyphenyl]propyl)piperidine,
4-(2-[p-methoxyphenyl]ethyl)piperidine,
4-(4-[m-methoxyphenyl]butyl)piperidine,
4-(3-[p-tolyl]propyl)piperidine,
4-(5-[m-methoxyphenyl]pentyl)piperidine,
4-(4-phenylbutyl)piperidine
4-(5-phenylpentyl)piperidine,
4-(2-phenylprop-1-yl)piperidine and
4-(2-phenylbut-1-yl)piperidine, respectively.

PREPARATION J

4-(3-Phenylpropyl)piperidinocarbonyl Chloride

Phosgene is passed into 150 ml. of dry toluene at 0°C. until 17 g. of gas has been absorbed. The cooling bath is removed, and to the phosgene solution is added, dropwise, with stirring, during 1 hour, a solution prepared from 27.6 g. of 4-(3-phenylpropyl)piperidine, and 12.3 ml. of pyridine and 100 ml. of toluene. After the end of the addition, the reaction mixture is stored at ambient temperature for 16 hours. At this point, the reaction mixture is filtered, and the filtrate is evaporated in vacuo, leaving 39 g. of the title compound in crude state. The product is contaminated with toluene, but it is sufficiently pure for coupling with alkenesulfonamides.

What is claimed is:

1. A compound selected from the group consisting of

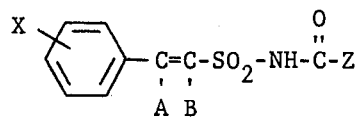

and the salts thereof;
wherein
X is selected from the group consisting of hydrogen, chloro and methyl;
A and B are each selected from the group consisting of hydrogen, methyl and ethyl;
and Z is selected from the group consisting of 4-methoxypiperidino, 4-carboxypiperidino, 4-phenylpiperidino, alkylpiperidino having from one to three carbon atoms in said alkyl group, (phenylalkyl)piperidino having from one to five carbon atoms in said alkyl group and ([substituted phenyl]-alkyl)piperidino having from one to five carbon atoms in said alkyl group, said substituted phenyl being substituted by a moiety selected from the group consisting of hydroxy, alkyl having from one to four carbon atoms and alkoxy having from one to four carbon atoms.

2. A compound according to claim 1, wherein A and B are each hydrogen.

3. A compound according to claim 2, wherein Z is selected from the group consisting of 4-(ω-phenylalkyl)piperidino having from one to five carbon atoms in said alkyl group and 4-(ω-[substituted phenyl]alkyl)-piperidino having from one to five carbon atoms in said alkyl group, said substituted phenyl being substituted by a moiety selected from the group consisting of hydroxy, alkyl having from one to four carbon atoms and alkoxy having from one to four carbon atoms.

4. A compound according to claim 3, wherein Z is the said 4-(ω-phenylalkyl)piperidino.

5. A compound according to claim 4, wherein X is hydrogen.

6. The compound according to claim 5, wherein Z is 4-(3-phenylpropyl)piperidino.

* * * * *